United States Patent
Ernst et al.

(10) Patent No.: US 10,004,462 B2
(45) Date of Patent: Jun. 26, 2018

(54) SYSTEMS, METHODS, AND DEVICES FOR REMOVING PROSPECTIVE MOTION CORRECTION FROM MEDICAL IMAGING SCANS

(71) Applicants: KinetiCor, Inc., Honolulu, HI (US); The University of Hawai'i, Honolulu, HI (US); The Queen's Medical Center, Honolulu, HI (US)

(72) Inventors: Thomas Michael Ernst, Honolulu, HI (US); Benjamin Anton Zahneisen, Ottensoos (DE); Jeffrey N. Yu, Honolulu, HI (US)

(73) Assignees: KinetiCor, Inc., Honolulu, HI (US); The University of Hawai'i, Honolulu, HI (US); The Queen's Medical Center, Honolulu, HI (US)

( * ) Notice: Subject to any disclaimer, the term of this patent is extended or adjusted under 35 U.S.C. 154(b) by 704 days.

(21) Appl. No.: 14/666,049

(22) Filed: Mar. 23, 2015

(65) Prior Publication Data

US 2015/0265220 A1    Sep. 24, 2015

Related U.S. Application Data

(60) Provisional application No. 61/969,765, filed on Mar. 24, 2014.

(51) Int. Cl.
*A61B 5/05* (2006.01)
*A61B 5/00* (2006.01)
(Continued)

(52) U.S. Cl.
CPC ............ *A61B 5/721* (2013.01); *A61B 5/0013* (2013.01); *A61B 5/055* (2013.01); *A61B 6/032* (2013.01);
(Continued)

(58) Field of Classification Search
CPC .......... G01R 33/5673; G01R 33/56509; G01R 33/565; G01R 33/56383; G01R 33/56391
(Continued)

(56) References Cited

U.S. PATENT DOCUMENTS

| 3,811,213 A | 5/1974 | Eaves |
| 4,689,999 A | 9/1987 | Shkedi |

(Continued)

FOREIGN PATENT DOCUMENTS

| CN | 105392423 | 3/2016 |
| DE | 29519078 | 3/1996 |

(Continued)

OTHER PUBLICATIONS

International Preliminary Report on Patentability for Application No. PCT/US2014/013546, dated Aug. 4, 2015, in 9 pages.
(Continued)

*Primary Examiner* — James Kish
(74) *Attorney, Agent, or Firm* — Knobbe, Martens, Olson & Bear LLP

(57) ABSTRACT

The disclosure herein provides methods, systems, and devices for removing prospective motion correction from medical imaging scans. In an embodiment, a computer-implemented method for removing motion correction from biomedical imaging scan data comprises tracking, by a computer system, motion of an object being scanned; generating, by the computer system, motion tracking data; adjusting, by the computer system, a biomedical imaging scanner, using the motion tracking data, to compensate in real time for object motion, such that raw image data generated by the scanner can be reconstructed into motion-corrected images; inverting, by the computer system, the motion tracking data; and applying, by the computer system, the inverted motion tracking data to the raw image data to
(Continued)

generate de-corrected image data representative of what the scanner would produce had the scanner not compensated for motion, wherein the de-corrected image data can be reconstructed into de-corrected images, wherein the computer system comprises an electronic memory and a computer processor.

28 Claims, 12 Drawing Sheets

(51) Int. Cl.

| | | |
|---|---|---|
| *A61B 5/055* | (2006.01) | |
| *A61B 6/03* | (2006.01) | |
| *G06T 5/00* | (2006.01) | |
| *G06T 5/50* | (2006.01) | |
| *A61B 6/00* | (2006.01) | |
| *A61B 34/20* | (2016.01) | |

(52) U.S. Cl.
CPC ............ *A61B 6/463* (2013.01); *A61B 6/5205* (2013.01); *A61B 6/527* (2013.01); *G06T 5/003* (2013.01); *G06T 5/50* (2013.01); *A61B 2034/2065* (2016.02); *A61B 2560/0475* (2013.01); *A61B 2560/0487* (2013.01); *A61B 2576/00* (2013.01); *A61B 2576/026* (2013.01); *G06T 2207/10081* (2013.01); *G06T 2207/10088* (2013.01); *G06T 2207/30016* (2013.01)

(58) Field of Classification Search
USPC .......................................... 600/410–423, 425
See application file for complete search history.

(56) References Cited

U.S. PATENT DOCUMENTS

| | | |
|---|---|---|
| 4,724,386 A | 2/1988 | Haacke et al. |
| 4,894,129 A | 1/1990 | Leiponen et al. |
| 4,923,295 A | 5/1990 | Sireul et al. |
| 4,953,554 A | 9/1990 | Zerhouni et al. |
| 4,988,886 A | 1/1991 | Palum et al. |
| 5,075,562 A | 12/1991 | Greivenkamp et al. |
| 5,318,026 A | 6/1994 | Pelc |
| 5,515,711 A | 5/1996 | Hinkle |
| 5,545,993 A | 8/1996 | Taguchi et al. |
| 5,615,677 A | 4/1997 | Pelc et al. |
| 5,687,725 A | 11/1997 | Wendt |
| 5,728,935 A | 3/1998 | Czompo |
| 5,802,202 A | 9/1998 | Yamada et al. |
| 5,835,223 A | 11/1998 | Zawemer et al. |
| 5,886,257 A | 3/1999 | Gustafson et al. |
| 5,889,505 A | 3/1999 | Toyama |
| 5,936,722 A | 8/1999 | Armstrong et al. |
| 5,936,723 A | 8/1999 | Schmidt et al. |
| 5,947,900 A | 9/1999 | Derbyshire et al. |
| 5,987,349 A | 11/1999 | Schulz |
| 6,031,888 A | 2/2000 | Ivan et al. |
| 6,044,308 A | 3/2000 | Huissoon |
| 6,057,680 A | 5/2000 | Foo et al. |
| 6,061,644 A | 5/2000 | Leis |
| 6,088,482 A | 7/2000 | He |
| 6,144,875 A | 11/2000 | Schweikard et al. |
| 6,236,737 B1 | 5/2001 | Gregson et al. |
| 6,246,900 B1 | 6/2001 | Cosman et al. |
| 6,279,579 B1 | 8/2001 | Riaziat et al. |
| 6,285,902 B1 | 9/2001 | Kienzle, III et al. |
| 6,289,235 B1 | 9/2001 | Webber |
| 6,292,683 B1 | 9/2001 | Gupta et al. |
| 6,298,262 B1 | 10/2001 | Franck et al. |
| 6,381,485 B1 | 4/2002 | Hunter et al. |
| 6,384,908 B1 | 5/2002 | Schmidt et al. |
| 6,390,982 B1 | 5/2002 | Bova et al. |
| 6,402,762 B2 | 6/2002 | Hunter et al. |
| 6,405,072 B1 | 6/2002 | Cosman |
| 6,421,551 B1 | 7/2002 | Kuth et al. |
| 6,467,905 B1 | 10/2002 | Stahl et al. |
| 6,474,159 B1 | 11/2002 | Foxlin et al. |
| 6,484,131 B1 | 11/2002 | Amoral-Moriya et al. |
| 6,490,475 B1 | 12/2002 | Seeley et al. |
| 6,501,981 B1 | 12/2002 | Schweikard et al. |
| 6,587,707 B2 | 7/2003 | Nehrke et al. |
| 6,621,889 B1 | 9/2003 | Mostafavi |
| 6,650,920 B2 | 11/2003 | Schaldach et al. |
| 6,662,036 B2 | 12/2003 | Cosman |
| 6,687,528 B2 | 2/2004 | Gupta et al. |
| 6,690,965 B1 | 2/2004 | Riaziat et al. |
| 6,711,431 B2 | 3/2004 | Sarin et al. |
| 6,731,970 B2 | 5/2004 | Schlossbauer et al. |
| 6,758,218 B2 | 7/2004 | Anthony |
| 6,771,997 B2 | 8/2004 | Schaffer |
| 6,794,869 B2 | 9/2004 | Brittain |
| 6,856,827 B2 | 2/2005 | Seeley et al. |
| 6,856,828 B2 | 2/2005 | Cossette et al. |
| 6,876,198 B2 | 4/2005 | Watanabe et al. |
| 6,888,924 B2 | 5/2005 | Claus et al. |
| 6,891,374 B2 | 5/2005 | Brittain |
| 6,892,089 B1 | 5/2005 | Prince et al. |
| 6,897,655 B2 | 5/2005 | Brittain et al. |
| 6,913,603 B2 | 7/2005 | Knopp et al. |
| 6,937,696 B1 | 8/2005 | Mostafavi |
| 6,959,266 B1 | 10/2005 | Mostafavi |
| 6,973,202 B2 | 12/2005 | Mostafavi |
| 6,980,679 B2 | 12/2005 | Jeung et al. |
| 7,007,699 B2 | 3/2006 | Martinelli et al. |
| 7,107,091 B2 | 9/2006 | Jutras et al. |
| 7,110,805 B2 | 9/2006 | Machida |
| 7,123,758 B2 | 10/2006 | Jeung et al. |
| 7,171,257 B2 | 1/2007 | Thomson |
| 7,176,440 B2 | 2/2007 | Cofer et al. |
| 7,191,100 B2 | 3/2007 | Mostafavi |
| 7,204,254 B2 | 4/2007 | Riaziat et al. |
| 7,209,777 B2 | 4/2007 | Saranathan et al. |
| 7,209,977 B2 | 4/2007 | Acharya et al. |
| 7,260,253 B2 | 8/2007 | Rahn et al. |
| 7,260,426 B2 | 8/2007 | Schweikard et al. |
| 7,295,007 B2 | 11/2007 | Dold |
| 7,313,430 B2 | 12/2007 | Urquhart et al. |
| 7,327,865 B2 | 2/2008 | Fu et al. |
| 7,348,776 B1 | 3/2008 | Aksoy et al. |
| 7,403,638 B2 | 7/2008 | Jeung et al. |
| 7,494,277 B2 | 2/2009 | Setala |
| 7,498,811 B2 | 3/2009 | Macfarlane et al. |
| 7,505,805 B2 | 3/2009 | Kuroda |
| 7,535,411 B2 | 5/2009 | Falco |
| 7,551,089 B2 | 6/2009 | Sawyer |
| 7,561,909 B1 | 7/2009 | Pai et al. |
| 7,567,697 B2 | 7/2009 | Mostafavi Hassan |
| 7,573,269 B2 | 8/2009 | Yao |
| 7,602,301 B1 | 10/2009 | Stirling et al. |
| 7,603,155 B2 | 10/2009 | Jensen |
| 7,623,623 B2 | 11/2009 | Raanes et al. |
| 7,657,300 B2 | 2/2010 | Hunter et al. |
| 7,657,301 B2 | 2/2010 | Mate et al. |
| 7,659,521 B2 | 2/2010 | Pedroni |
| 7,660,623 B2 | 2/2010 | Hunter et al. |
| 7,668,288 B2 | 2/2010 | Conwell et al. |
| 7,689,263 B1 | 3/2010 | Fung et al. |
| 7,702,380 B1 | 4/2010 | Dean |
| 7,715,604 B2 | 5/2010 | Sun et al. |
| 7,742,077 B2 | 6/2010 | Sablak et al. |
| 7,742,621 B2 | 6/2010 | Hammoud et al. |
| 7,742,804 B2 | 6/2010 | Faul et al. |
| 7,744,528 B2 | 6/2010 | Wallace et al. |
| 7,760,908 B2 | 7/2010 | Curtner et al. |
| 7,766,837 B2 | 8/2010 | Pedrizzetti et al. |
| 7,769,430 B2 | 8/2010 | Mostafavi |
| 7,772,569 B2 | 8/2010 | Bewersdorf et al. |
| 7,787,011 B2 | 8/2010 | Zhou et al. |
| 7,787,935 B2 | 8/2010 | Dumoulin et al. |
| 7,791,808 B2 | 9/2010 | French et al. |
| 7,792,249 B2 | 9/2010 | Gertner et al. |

(56) References Cited

U.S. PATENT DOCUMENTS

| | | |
|---|---|---|
| 7,796,154 B2 | 9/2010 | Senior et al. |
| 7,798,730 B2 | 9/2010 | Westerweck |
| 7,801,330 B2 | 9/2010 | Zhang et al. |
| 7,805,987 B1 | 10/2010 | Smith |
| 7,806,604 B2 | 10/2010 | Bazakos et al. |
| 7,817,046 B2 | 10/2010 | Coveley et al. |
| 7,817,824 B2 | 10/2010 | Liang et al. |
| 7,819,818 B2 | 10/2010 | Ghajar |
| 7,833,221 B2 | 11/2010 | Voegele |
| 7,834,846 B1 | 11/2010 | Bell |
| 7,835,783 B1 | 11/2010 | Aletras |
| 7,839,551 B2 | 11/2010 | Lee et al. |
| 7,840,253 B2 | 11/2010 | Tremblay et al. |
| 7,844,094 B2 | 11/2010 | Jeung et al. |
| 7,844,320 B2 | 11/2010 | Shahidi |
| 7,850,526 B2 | 12/2010 | Zalewski et al. |
| 7,860,301 B2 | 12/2010 | Se et al. |
| 7,866,818 B2 | 1/2011 | Schroeder et al. |
| 7,868,282 B2 | 1/2011 | Lee et al. |
| 7,878,652 B2 | 2/2011 | Chen et al. |
| 7,883,415 B2 | 2/2011 | Larsen et al. |
| 7,889,907 B2 | 2/2011 | Engelbart et al. |
| 7,894,877 B2 | 2/2011 | Lewin et al. |
| 7,902,825 B2 | 3/2011 | Bammer |
| 7,907,987 B2 | 3/2011 | Dempsey |
| 7,908,060 B2 | 3/2011 | Basson et al. |
| 7,908,233 B2 | 3/2011 | Angell et al. |
| 7,911,207 B2 | 3/2011 | Macfarlane et al. |
| 7,912,532 B2 | 3/2011 | Schmidt et al. |
| 7,920,250 B2 | 4/2011 | Robert et al. |
| 7,920,911 B2 | 4/2011 | Hoshino et al. |
| 7,925,066 B2 | 4/2011 | Ruohonen et al. |
| 7,925,549 B2 | 4/2011 | Looney et al. |
| 7,931,370 B2 | 4/2011 | Bartomen |
| 7,944,354 B2 | 5/2011 | Kangas et al. |
| 7,944,454 B2 | 5/2011 | Zhou et al. |
| 7,945,304 B2 | 5/2011 | Feinberg |
| 7,946,921 B2 | 5/2011 | Ofek et al. |
| 7,962,197 B2 | 6/2011 | Rioux et al. |
| 7,971,999 B2 | 7/2011 | Zinser |
| 7,977,942 B2 | 7/2011 | White |
| 7,978,925 B1 | 7/2011 | Souchard |
| 7,988,288 B2 | 8/2011 | Donaldson |
| 7,990,365 B2 | 8/2011 | Marvit et al. |
| 8,005,571 B2 | 8/2011 | Sutherland et al. |
| 8,009,198 B2 | 8/2011 | Alhadef |
| 8,019,170 B2 | 9/2011 | Wang et al. |
| 8,021,231 B2 | 9/2011 | Walker et al. |
| 8,022,982 B2 | 9/2011 | Thorn |
| 8,024,026 B2 | 9/2011 | Groszmann |
| 8,031,909 B2 | 10/2011 | Se et al. |
| 8,031,933 B2 | 10/2011 | Se et al. |
| 8,036,425 B2 | 10/2011 | Hou |
| 8,041,077 B2 | 10/2011 | Bell |
| 8,041,412 B2 | 10/2011 | Glossop et al. |
| 8,048,002 B2 | 11/2011 | Ghajar |
| 8,049,867 B2 | 11/2011 | Bridges et al. |
| 8,055,020 B2 | 11/2011 | Meuter et al. |
| 8,055,049 B2 | 11/2011 | Stayman et al. |
| 8,060,185 B2 | 11/2011 | Hunter et al. |
| 8,063,929 B2 | 11/2011 | Kurtz et al. |
| 8,073,197 B2 | 12/2011 | Xu et al. |
| 8,077,914 B1 | 12/2011 | Kaplan |
| 8,085,302 B2 | 12/2011 | Zhang et al. |
| 8,086,026 B2 | 12/2011 | Schulz |
| 8,086,299 B2 | 12/2011 | Adler et al. |
| RE43,147 E | 1/2012 | Aviv |
| 8,094,193 B2 | 1/2012 | Peterson |
| 8,095,203 B2 | 1/2012 | Wright et al. |
| 8,095,209 B2 | 1/2012 | Flaherty |
| 8,098,889 B2 | 1/2012 | Zhu et al. |
| 8,113,991 B2 | 2/2012 | Kutliroff |
| 8,116,527 B2 | 2/2012 | Sabol |
| 8,121,356 B2 | 2/2012 | Friedman |
| 8,121,361 B2 | 2/2012 | Ernst et al. |
| 8,134,597 B2 | 3/2012 | Thorn |
| 8,135,201 B2 | 3/2012 | Smith et al. |
| 8,139,029 B2 | 3/2012 | Boillot |
| 8,139,896 B1 | 3/2012 | Ahiska |
| 8,144,118 B2 | 3/2012 | Hildreth |
| 8,144,148 B2 | 3/2012 | El Dokor |
| 8,150,063 B2 | 4/2012 | Chen |
| 8,150,498 B2 | 4/2012 | Gielen et al. |
| 8,160,304 B2 | 4/2012 | Rhoads |
| 8,165,844 B2 | 4/2012 | Luinge et al. |
| 8,167,802 B2 | 5/2012 | Baba et al. |
| 8,172,573 B2 | 5/2012 | Sonenfeld et al. |
| 8,175,332 B2 | 5/2012 | Harrington |
| 8,179,604 B1 | 5/2012 | Prada Gomez |
| 8,180,428 B2 | 5/2012 | Kaiser et al. |
| 8,180,432 B2 | 5/2012 | Sayeh |
| 8,187,097 B1 | 5/2012 | Zhang |
| 8,189,869 B2 | 5/2012 | Bell |
| 8,189,889 B2 | 5/2012 | Pearlstein et al. |
| 8,189,926 B2 | 5/2012 | Sharma |
| 8,190,233 B2 | 5/2012 | Dempsey |
| 8,191,359 B2 | 6/2012 | White et al. |
| 8,194,134 B2 | 6/2012 | Furukawa |
| 8,195,084 B2 | 6/2012 | Xiao |
| 8,199,983 B2 | 6/2012 | Qureshi |
| 8,206,219 B2 | 6/2012 | Shum |
| 8,207,967 B1 | 6/2012 | El Dokor |
| 8,208,758 B2 | 6/2012 | Wang |
| 8,213,693 B1 | 7/2012 | Li |
| 8,214,012 B2 | 7/2012 | Zuccolotto et al. |
| 8,214,016 B2 | 7/2012 | Lavallee et al. |
| 8,216,016 B2 | 7/2012 | Yamagishi et al. |
| 8,218,818 B2 | 7/2012 | Cobb |
| 8,218,819 B2 | 7/2012 | Cobb |
| 8,218,825 B2 | 7/2012 | Gordon |
| 8,221,399 B2 | 7/2012 | Amano |
| 8,223,147 B1 | 7/2012 | El Dokor |
| 8,224,423 B2 | 7/2012 | Faul |
| 8,226,574 B2 | 7/2012 | Whillock |
| 8,229,163 B2 | 7/2012 | Coleman |
| 8,229,166 B2 | 7/2012 | Teng |
| 8,229,184 B2 | 7/2012 | Benkley |
| 8,232,872 B2 | 7/2012 | Zeng |
| 8,235,529 B1 | 8/2012 | Raffle |
| 8,235,530 B2 | 8/2012 | Maad |
| 8,241,125 B2 | 8/2012 | Hughes |
| 8,243,136 B2 | 8/2012 | Aota |
| 8,243,269 B2 | 8/2012 | Matousek |
| 8,243,996 B2 | 8/2012 | Steinberg |
| 8,248,372 B2 | 8/2012 | Saila |
| 8,249,691 B2 | 8/2012 | Chase et al. |
| 8,253,770 B2 | 8/2012 | Kurtz |
| 8,253,774 B2 | 8/2012 | Huitema |
| 8,253,778 B2 | 8/2012 | Atsushi |
| 8,259,109 B2 | 9/2012 | El Dokor |
| 8,260,036 B2 | 9/2012 | Hamza et al. |
| 8,279,288 B2 | 10/2012 | Son |
| 8,284,157 B2 | 10/2012 | Markovic |
| 8,284,847 B2 | 10/2012 | Adermann |
| 8,287,373 B2 | 10/2012 | Marx |
| 8,289,390 B2 | 10/2012 | Aggarwal |
| 8,289,392 B2 | 10/2012 | Williams, Sr. |
| 8,290,208 B2 | 10/2012 | Kurtz |
| 8,290,229 B2 | 10/2012 | Qureshi |
| 8,295,573 B2 | 10/2012 | Bredno et al. |
| 8,301,226 B2 | 10/2012 | Csavoy et al. |
| 8,306,260 B2 | 11/2012 | Zhu |
| 8,306,267 B1 | 11/2012 | Gossweiler, III |
| 8,306,274 B2 | 11/2012 | Grycewicz |
| 8,306,663 B2 | 11/2012 | Wickham |
| 8,310,656 B2 | 11/2012 | Zalewski |
| 8,310,662 B2 | 11/2012 | Mehr |
| 8,311,611 B2 | 11/2012 | Csavoy et al. |
| 8,314,854 B2 | 11/2012 | Yoon |
| 8,315,691 B2 | 11/2012 | Sumanaweera et al. |
| 8,316,324 B2 | 11/2012 | Boillot |
| 8,320,621 B2 | 11/2012 | McEldowney |
| 8,320,709 B2 | 11/2012 | Arartani et al. |
| 8,323,106 B2 | 12/2012 | Zalewski |

(56) References Cited

U.S. PATENT DOCUMENTS

| | | |
|---|---|---|
| 8,325,228 B2 | 12/2012 | Mariadoss |
| 8,330,811 B2 | 12/2012 | Macguire, Jr. |
| 8,330,812 B2 | 12/2012 | Maguire, Jr. |
| 8,331,019 B2 | 12/2012 | Cheong |
| 8,334,900 B2 | 12/2012 | Qu et al. |
| 8,339,282 B2 | 12/2012 | Noble |
| 8,351,651 B2 | 1/2013 | Lee |
| 8,368,586 B2 | 2/2013 | Mohamadi |
| 8,369,574 B2 | 2/2013 | Atu |
| 8,374,393 B2 | 2/2013 | Cobb |
| 8,374,411 B2 | 2/2013 | Ernst et al. |
| 8,374,674 B2 | 2/2013 | Gertner |
| 8,376,226 B2 | 2/2013 | Dennard |
| 8,376,827 B2 | 2/2013 | Cammegh |
| 8,379,927 B2 | 2/2013 | Taylor |
| 8,380,284 B2 | 2/2013 | Saranathan et al. |
| 8,386,011 B2 | 2/2013 | Wieczorek |
| 8,390,291 B2 | 3/2013 | Macfarlane et al. |
| 8,390,729 B2 | 3/2013 | Long |
| 8,395,620 B2 | 3/2013 | El Dokor |
| 8,396,654 B1 | 3/2013 | Simmons et al. |
| 8,400,398 B2 | 3/2013 | Schoen |
| 8,400,490 B2 | 3/2013 | Apostolopoulos |
| 8,405,491 B2 | 3/2013 | Fong |
| 8,405,656 B2 | 3/2013 | El Dokor |
| 8,405,717 B2 | 3/2013 | Kim |
| 8,406,845 B2 | 3/2013 | Komistek et al. |
| 8,411,931 B2 | 4/2013 | Zhou |
| 8,427,538 B2 | 4/2013 | Ahiska |
| 8,428,319 B2 | 4/2013 | Tsin et al. |
| 8,571,293 B2 | 10/2013 | Ernst et al. |
| 8,615,127 B2 | 12/2013 | Fitzpatrick |
| 8,744,154 B2 | 6/2014 | Van Den Brink |
| 8,848,977 B2 | 9/2014 | Bammer et al. |
| 8,862,420 B2 | 10/2014 | Ferran et al. |
| 8,953,847 B2 | 2/2015 | Moden |
| 8,996,094 B2 | 3/2015 | Schouenborg et al. |
| 9,076,212 B2 | 7/2015 | Ernst et al. |
| 9,082,177 B2 | 7/2015 | Sebok |
| 9,084,629 B1 | 7/2015 | Rosa |
| 9,103,897 B2 | 8/2015 | Herbst et al. |
| 9,138,175 B2 | 9/2015 | Ernst et al. |
| 9,173,715 B2 | 11/2015 | Baumgartner |
| 9,176,932 B2 | 11/2015 | Baggen et al. |
| 9,194,929 B2 | 11/2015 | Siegert et al. |
| 9,305,365 B2 | 4/2016 | Lovberg et al. |
| 9,395,386 B2 | 7/2016 | Corder et al. |
| 9,451,926 B2 | 9/2016 | Kinahan et al. |
| 9,606,209 B2 | 3/2017 | Ernst et al. |
| 9,607,377 B2 | 3/2017 | Lovberg et al. |
| 2002/0082496 A1 | 6/2002 | Kuth |
| 2002/0091422 A1 | 7/2002 | Greenberg et al. |
| 2002/0115931 A1 | 8/2002 | Strauss et al. |
| 2002/0180436 A1 | 12/2002 | Dale et al. |
| 2002/0188194 A1 | 12/2002 | Cosman |
| 2003/0063292 A1 | 4/2003 | Mostafavi |
| 2003/0088177 A1 | 5/2003 | Totterman et al. |
| 2003/0116166 A1 | 6/2003 | Anthony |
| 2003/0130574 A1 | 7/2003 | Stoyle |
| 2004/0071324 A1 | 4/2004 | Norris et al. |
| 2004/0116804 A1 | 6/2004 | Mostafavi |
| 2004/0140804 A1 | 7/2004 | Polzin et al. |
| 2004/0171927 A1* | 9/2004 | Lowen .................. A61B 5/055 600/410 |
| 2005/0027194 A1 | 2/2005 | Adler et al. |
| 2005/0054910 A1 | 3/2005 | Tremblay et al. |
| 2005/0070784 A1* | 3/2005 | Komura .................. A61B 5/055 600/410 |
| 2005/0105772 A1 | 5/2005 | Voronka et al. |
| 2005/0107685 A1 | 5/2005 | Seeber |
| 2005/0137475 A1* | 6/2005 | Dold .................... A61B 5/055 600/414 |
| 2005/0148854 A1 | 7/2005 | Ito et al. |
| 2005/0283068 A1 | 12/2005 | Zuccoloto et al. |
| 2006/0004281 A1 | 1/2006 | Saracen |
| 2006/0045310 A1 | 3/2006 | Tu et al. |
| 2006/0074292 A1 | 4/2006 | Thomson et al. |
| 2006/0241405 A1 | 10/2006 | Leitner et al. |
| 2007/0093709 A1 | 4/2007 | Abernathie |
| 2007/0206836 A1 | 9/2007 | Yoon |
| 2007/0239169 A1 | 10/2007 | Plaskos et al. |
| 2007/0280508 A1 | 12/2007 | Ernst et al. |
| 2008/0039713 A1 | 2/2008 | Thomson et al. |
| 2008/0181358 A1 | 7/2008 | Van Kampen et al. |
| 2008/0183074 A1 | 7/2008 | Carls et al. |
| 2008/0212835 A1 | 9/2008 | Tavor |
| 2008/0221442 A1 | 9/2008 | Tolowsky et al. |
| 2008/0273754 A1 | 11/2008 | Hick et al. |
| 2008/0287728 A1 | 11/2008 | QUERY |
| 2008/0287780 A1 | 11/2008 | Chase et al. |
| 2008/0317313 A1 | 12/2008 | Goddard et al. |
| 2009/0028411 A1 | 1/2009 | Pfeuffer |
| 2009/0052760 A1 | 2/2009 | Smith et al. |
| 2009/0185663 A1 | 7/2009 | Gaines, Jr. et al. |
| 2009/0209846 A1* | 8/2009 | Bammer .................. A61B 5/055 600/421 |
| 2009/0253985 A1 | 10/2009 | Shachar et al. |
| 2009/0304297 A1 | 12/2009 | Adabala et al. |
| 2009/0306499 A1 | 12/2009 | Van Vorhis et al. |
| 2010/0054579 A1 | 3/2010 | Okutomi |
| 2010/0057059 A1 | 3/2010 | Makino |
| 2010/0059679 A1 | 3/2010 | Albrecht |
| 2010/0069742 A1 | 3/2010 | Partain et al. |
| 2010/0091089 A1 | 4/2010 | Cromwell et al. |
| 2010/0099981 A1 | 4/2010 | Fishel |
| 2010/0125191 A1 | 5/2010 | Sahin |
| 2010/0137709 A1 | 6/2010 | Gardner et al. |
| 2010/0148774 A1 | 6/2010 | Kamata |
| 2010/0149099 A1 | 6/2010 | Elias |
| 2010/0149315 A1 | 6/2010 | Qu |
| 2010/0160775 A1 | 6/2010 | Pankratov |
| 2010/0164862 A1 | 7/2010 | Sullivan |
| 2010/0165293 A1 | 7/2010 | Tanassi et al. |
| 2010/0167246 A1 | 7/2010 | Ghajar |
| 2010/0172567 A1 | 7/2010 | Prokoski |
| 2010/0177929 A1 | 7/2010 | Kurtz |
| 2010/0178966 A1 | 7/2010 | Seydoux |
| 2010/0179390 A1 | 7/2010 | Davis |
| 2010/0179413 A1 | 7/2010 | Kadour et al. |
| 2010/0183196 A1 | 7/2010 | Fu et al. |
| 2010/0191631 A1 | 7/2010 | Weidmann |
| 2010/0194879 A1 | 8/2010 | Pasveer |
| 2010/0198067 A1 | 8/2010 | Mahfouz |
| 2010/0198101 A1 | 8/2010 | Song |
| 2010/0198112 A1 | 8/2010 | Maad |
| 2010/0199232 A1 | 8/2010 | Mistry |
| 2010/0210350 A9 | 8/2010 | Walker |
| 2010/0214267 A1 | 8/2010 | Radivojevic |
| 2010/0231511 A1 | 9/2010 | Henty |
| 2010/0231692 A1 | 9/2010 | Perlman |
| 2010/0245536 A1 | 9/2010 | Huitema |
| 2010/0245593 A1 | 9/2010 | Kim |
| 2010/0251924 A1 | 10/2010 | Taylor |
| 2010/0253762 A1 | 10/2010 | Cheong |
| 2010/0268072 A1 | 10/2010 | Hall et al. |
| 2010/0277571 A1 | 11/2010 | Xu |
| 2010/0282902 A1 | 11/2010 | Indraeswaran |
| 2010/0283833 A1 | 11/2010 | Yeh |
| 2010/0284119 A1 | 11/2010 | Coakley |
| 2010/0289899 A1 | 11/2010 | Hendron |
| 2010/0290668 A1 | 11/2010 | Friedman |
| 2010/0292841 A1 | 11/2010 | Wickham |
| 2010/0295718 A1 | 11/2010 | Mohamadi |
| 2010/0296701 A1 | 11/2010 | Hu |
| 2010/0302142 A1 | 12/2010 | French |
| 2010/0303289 A1 | 12/2010 | Polzin |
| 2010/0311512 A1 | 12/2010 | Lock |
| 2010/0321505 A1 | 12/2010 | Kokubun |
| 2010/0328055 A1 | 12/2010 | Fong |
| 2010/0328201 A1 | 12/2010 | Marbit |
| 2010/0328267 A1 | 12/2010 | Chen |
| 2010/0330912 A1 | 12/2010 | Saila |
| 2011/0001699 A1 | 1/2011 | Jacobsen |
| 2011/0006991 A1 | 1/2011 | Elias |

(56) References Cited

U.S. PATENT DOCUMENTS

| | | |
|---|---|---|
| 2011/0007939 A1 | 1/2011 | Teng |
| 2011/0007946 A1 | 1/2011 | Liang |
| 2011/0008759 A1 | 1/2011 | Usui |
| 2011/0015521 A1 | 1/2011 | Faul |
| 2011/0019001 A1 | 1/2011 | Rhoads |
| 2011/0025853 A1 | 2/2011 | Richardson |
| 2011/0038520 A1 | 2/2011 | Yui |
| 2011/0043631 A1 | 2/2011 | Marman |
| 2011/0043759 A1 | 2/2011 | Bushinsky |
| 2011/0050562 A1 | 3/2011 | Schoen |
| 2011/0050569 A1 | 3/2011 | Marvit |
| 2011/0050947 A1 | 3/2011 | Marman |
| 2011/0052002 A1 | 3/2011 | Cobb |
| 2011/0052003 A1 | 3/2011 | Cobb |
| 2011/0052015 A1 | 3/2011 | Saund |
| 2011/0054870 A1 | 3/2011 | Dariush |
| 2011/0057816 A1 | 3/2011 | Noble |
| 2011/0058020 A1 | 3/2011 | Dieckmann |
| 2011/0069207 A1 | 3/2011 | Steinberg |
| 2011/0074675 A1 | 3/2011 | Shiming |
| 2011/0081000 A1 | 4/2011 | Gertner |
| 2011/0081043 A1 | 4/2011 | Sabol |
| 2011/0085704 A1 | 4/2011 | Han |
| 2011/0092781 A1 | 4/2011 | Gertner |
| 2011/0102549 A1 | 5/2011 | Takahashi |
| 2011/0105883 A1 | 5/2011 | Lake et al. |
| 2011/0105893 A1 | 5/2011 | Akins |
| 2011/0115793 A1 | 5/2011 | Grycewicz |
| 2011/0115892 A1 | 5/2011 | Fan |
| 2011/0116683 A1 | 5/2011 | Kramer et al. |
| 2011/0117528 A1 | 5/2011 | Marciello et al. |
| 2011/0118032 A1 | 5/2011 | Zalewski |
| 2011/0133917 A1 | 6/2011 | Zeng |
| 2011/0142411 A1 | 6/2011 | Camp |
| 2011/0150271 A1 | 6/2011 | Lee |
| 2011/0157168 A1 | 6/2011 | Bennett |
| 2011/0157358 A1 | 6/2011 | Bell |
| 2011/0157370 A1 | 6/2011 | Livesey |
| 2011/0160569 A1 | 6/2011 | Cohen et al. |
| 2011/0172060 A1 | 7/2011 | Morales |
| 2011/0172521 A1 | 7/2011 | Zdeblick et al. |
| 2011/0175801 A1 | 7/2011 | Markovic |
| 2011/0175809 A1 | 7/2011 | Markovic |
| 2011/0175810 A1 | 7/2011 | Markovic |
| 2011/0176723 A1 | 7/2011 | Ali et al. |
| 2011/0180695 A1 | 7/2011 | Li |
| 2011/0181893 A1 | 7/2011 | MacFarlane |
| 2011/0182472 A1 | 7/2011 | Hansen |
| 2011/0187640 A1 | 8/2011 | Jacobsen |
| 2011/0193939 A1 | 8/2011 | Vassigh |
| 2011/0199461 A1 | 8/2011 | Horio |
| 2011/0201916 A1 | 8/2011 | Duyn et al. |
| 2011/0201939 A1 | 8/2011 | Hubschman et al. |
| 2011/0202306 A1 | 8/2011 | Eng |
| 2011/0205358 A1 | 8/2011 | Aota |
| 2011/0207089 A1 | 8/2011 | Lagettie |
| 2011/0208437 A1 | 8/2011 | Teicher |
| 2011/0216002 A1 | 9/2011 | Weising |
| 2011/0216180 A1 | 9/2011 | Pasini |
| 2011/0221770 A1 | 9/2011 | Kruglick |
| 2011/0229862 A1 | 9/2011 | Parikh |
| 2011/0230755 A1 | 9/2011 | MacFarlane et al. |
| 2011/0234807 A1 | 9/2011 | Jones |
| 2011/0234834 A1 | 9/2011 | Sugimoto |
| 2011/0235855 A1 | 9/2011 | Smith |
| 2011/0237933 A1 | 9/2011 | Cohen |
| 2011/0242134 A1 | 10/2011 | Miller |
| 2011/0244939 A1 | 10/2011 | Cammegh |
| 2011/0250929 A1 | 10/2011 | Lin |
| 2011/0251478 A1 | 10/2011 | Wieczorek |
| 2011/0255845 A1 | 10/2011 | Kikuchi |
| 2011/0257566 A1 | 10/2011 | Burdea |
| 2011/0260965 A1 | 10/2011 | Kim |
| 2011/0262002 A1 | 10/2011 | Lee |
| 2011/0267427 A1 | 11/2011 | Goh |
| 2011/0267456 A1 | 11/2011 | Adermann |
| 2011/0275957 A1 | 11/2011 | Bhandari |
| 2011/0276396 A1 | 11/2011 | Rathod |
| 2011/0279663 A1 | 11/2011 | Fan |
| 2011/0285622 A1 | 11/2011 | Marti |
| 2011/0286010 A1 | 11/2011 | Kusik et al. |
| 2011/0291925 A1 | 12/2011 | Israel |
| 2011/0293143 A1 | 12/2011 | Narayanan et al. |
| 2011/0293146 A1 | 12/2011 | Grycewicz |
| 2011/0298708 A1 | 12/2011 | Hsu |
| 2011/0298824 A1 | 12/2011 | Lee |
| 2011/0300994 A1 | 12/2011 | Verkaaik |
| 2011/0301449 A1 | 12/2011 | Maurer, Jr. |
| 2011/0301934 A1 | 12/2011 | Tardis |
| 2011/0303214 A1 | 12/2011 | Welle |
| 2011/0304541 A1 | 12/2011 | Dalal |
| 2011/0304650 A1 | 12/2011 | Canpillo |
| 2011/0304706 A1 | 12/2011 | Porter |
| 2011/0306867 A1 | 12/2011 | Gopinathan |
| 2011/0310220 A1 | 12/2011 | McEldowney |
| 2011/0310226 A1 | 12/2011 | McEldowney |
| 2011/0316994 A1 | 12/2011 | Lemchen |
| 2011/0317877 A1 | 12/2011 | Bell |
| 2012/0002112 A1 | 1/2012 | Huang |
| 2012/0004791 A1 | 1/2012 | Buelthoff |
| 2012/0007839 A1 | 1/2012 | Tsao et al. |
| 2012/0019645 A1 | 1/2012 | Maltz |
| 2012/0020524 A1 | 1/2012 | Ishikawa |
| 2012/0021806 A1 | 1/2012 | Naltz |
| 2012/0027226 A1 | 2/2012 | Desenberg |
| 2012/0029345 A1 | 2/2012 | Mahfouz et al. |
| 2012/0032882 A1 | 2/2012 | Schlachta |
| 2012/0033083 A1 | 2/2012 | Horvinger |
| 2012/0035462 A1 | 2/2012 | Maurer, Jr. et al. |
| 2012/0039505 A1 | 2/2012 | Vastide |
| 2012/0044363 A1 | 2/2012 | Lu |
| 2012/0045091 A1 | 2/2012 | Kaganovich |
| 2012/0049453 A1 | 3/2012 | Morichau-Beauchant |
| 2012/0051588 A1 | 3/2012 | McEldowney |
| 2012/0051664 A1 | 3/2012 | Gopalakrishnan et al. |
| 2012/0052949 A1 | 3/2012 | Weitzner |
| 2012/0056982 A1 | 3/2012 | Katz |
| 2012/0057640 A1 | 3/2012 | Shi |
| 2012/0065492 A1 | 3/2012 | Gertner et al. |
| 2012/0065494 A1 | 3/2012 | Gertner et al. |
| 2012/0072041 A1 | 3/2012 | Miller |
| 2012/0075166 A1 | 3/2012 | Marti |
| 2012/0075177 A1 | 3/2012 | Jacobsen |
| 2012/0076369 A1 | 3/2012 | Abramovich |
| 2012/0081504 A1 | 4/2012 | Ng |
| 2012/0083314 A1 | 4/2012 | Ng |
| 2012/0083960 A1 | 4/2012 | Zhu |
| 2012/0086778 A1 | 4/2012 | Lee |
| 2012/0086809 A1 | 4/2012 | Lee |
| 2012/0092445 A1 | 4/2012 | McDowell |
| 2012/0092502 A1 | 4/2012 | Knasel |
| 2012/0093481 A1 | 4/2012 | McDowell |
| 2012/0098938 A1 | 4/2012 | Jin |
| 2012/0101388 A1 | 4/2012 | Tripathi |
| 2012/0105573 A1 | 5/2012 | Apostolopoulos |
| 2012/0106814 A1 | 5/2012 | Gleason et al. |
| 2012/0108909 A1 | 5/2012 | Soobounob |
| 2012/0113140 A1 | 5/2012 | Hilliges |
| 2012/0113223 A1 | 5/2012 | Hilliges |
| 2012/0116202 A1 | 5/2012 | Bangera |
| 2012/0119999 A1 | 5/2012 | Harris |
| 2012/0120072 A1 | 5/2012 | Se |
| 2012/0120237 A1 | 5/2012 | Trepess |
| 2012/0120243 A1 | 5/2012 | Chien |
| 2012/0120277 A1 | 5/2012 | Tsai |
| 2012/0121124 A1 | 5/2012 | Bammer |
| 2012/0124604 A1 | 5/2012 | Small |
| 2012/0127319 A1 | 5/2012 | Rao |
| 2012/0133616 A1 | 5/2012 | Nishihara |
| 2012/0133889 A1 | 5/2012 | Bergt |
| 2012/0143029 A1 | 6/2012 | Silverstein |
| 2012/0143212 A1 | 6/2012 | Madhani |
| 2012/0154272 A1 | 6/2012 | Hildreth |
| 2012/0154511 A1 | 6/2012 | Hsu |

(56) References Cited

U.S. PATENT DOCUMENTS

| | | |
|---|---|---|
| 2012/0154536 A1 | 6/2012 | Stoker |
| 2012/0154579 A1 | 6/2012 | Hanpapur |
| 2012/0156661 A1 | 6/2012 | Smith |
| 2012/0158197 A1 | 6/2012 | Hinman |
| 2012/0162378 A1 | 6/2012 | El Dokor |
| 2012/0165964 A1 | 6/2012 | Flaks |
| 2012/0167143 A1 | 6/2012 | Longet |
| 2012/0169841 A1 | 7/2012 | Chemali |
| 2012/0176314 A1 | 7/2012 | Jeon |
| 2012/0184371 A1 | 7/2012 | Shum |
| 2012/0188237 A1 | 7/2012 | Han |
| 2012/0188371 A1 | 7/2012 | Chen |
| 2012/0194422 A1 | 8/2012 | El Dokor |
| 2012/0194517 A1 | 8/2012 | Ivadi |
| 2012/0194561 A1 | 8/2012 | Grossinger |
| 2012/0195466 A1 | 8/2012 | Teng |
| 2012/0196660 A1 | 8/2012 | Eo Dokor |
| 2012/0197135 A1 | 8/2012 | Slatkine |
| 2012/0200676 A1 | 8/2012 | Huitema |
| 2012/0201428 A1 | 8/2012 | Joshi et al. |
| 2012/0206604 A1 | 8/2012 | Jones |
| 2012/0212594 A1 | 8/2012 | Barns |
| 2012/0218407 A1 | 8/2012 | Chien |
| 2012/0218421 A1 | 8/2012 | Chien |
| 2012/0220233 A1 | 8/2012 | Teague |
| 2012/0224666 A1 | 9/2012 | Speller |
| 2012/0224743 A1 | 9/2012 | Rodriguez |
| 2012/0225718 A1 | 9/2012 | Zhang |
| 2012/0229643 A1 | 9/2012 | Chidanand |
| 2012/0229651 A1 | 9/2012 | Takizawa |
| 2012/0230561 A1 | 9/2012 | Qureshi |
| 2012/0235896 A1 | 9/2012 | Jacobsen |
| 2012/0238337 A1 | 9/2012 | French |
| 2012/0242816 A1 | 9/2012 | Cruz |
| 2012/0249741 A1 | 10/2012 | Maciocci |
| 2012/0253201 A1 | 10/2012 | Reinhold |
| 2012/0253241 A1 | 10/2012 | Ludital |
| 2012/0262540 A1 | 10/2012 | Rondinelli |
| 2012/0262558 A1 | 10/2012 | Boger |
| 2012/0262583 A1 | 10/2012 | Bernal |
| 2012/0268124 A1 | 10/2012 | Herbst et al. |
| 2012/0275649 A1 | 11/2012 | Cobb |
| 2012/0276995 A1 | 11/2012 | Lansdale |
| 2012/0277001 A1 | 11/2012 | Lansdale |
| 2012/0281093 A1 | 11/2012 | Fong |
| 2012/0281873 A1 | 11/2012 | Brown |
| 2012/0288142 A1 | 11/2012 | Gossweiler, III |
| 2012/0288852 A1 | 11/2012 | Willson |
| 2012/0289334 A9 | 11/2012 | Mikhailov |
| 2012/0289822 A1 | 11/2012 | Shachar et al. |
| 2012/0293412 A1 | 11/2012 | El Dokor |
| 2012/0293506 A1 | 11/2012 | Vertucci |
| 2012/0293663 A1 | 11/2012 | Liu |
| 2012/0294511 A1 | 11/2012 | Datta |
| 2012/0300961 A1 | 11/2012 | Moeller |
| 2012/0303839 A1 | 11/2012 | Jackson |
| 2012/0304126 A1 | 11/2012 | Lavigne |
| 2012/0307075 A1 | 12/2012 | Margalit |
| 2012/0307207 A1 | 12/2012 | Abraham |
| 2012/0314066 A1 | 12/2012 | Lee |
| 2012/0315016 A1 | 12/2012 | Fung |
| 2012/0319946 A1 | 12/2012 | El Dokor |
| 2012/0319989 A1 | 12/2012 | Argiro |
| 2012/0320178 A1 | 12/2012 | Siegert et al. |
| 2012/0320219 A1 | 12/2012 | David |
| 2012/0326966 A1 | 12/2012 | Rauber |
| 2012/0326976 A1 | 12/2012 | Markovic |
| 2012/0326979 A1 | 12/2012 | Geisert |
| 2012/0327241 A1 | 12/2012 | Howe |
| 2012/0327246 A1 | 12/2012 | William, Sr. |
| 2013/0002866 A1 | 1/2013 | Hanpapur |
| 2013/0002879 A1 | 1/2013 | Weber |
| 2013/0002900 A1 | 1/2013 | Gossweiler, III |
| 2013/0009865 A1 | 1/2013 | Valik |
| 2013/0010071 A1 | 1/2013 | Valik |
| 2013/0013452 A1 | 1/2013 | Dennard |
| 2013/0016009 A1 | 1/2013 | Godfrey |
| 2013/0016876 A1 | 1/2013 | Wooley |
| 2013/0021434 A1 | 1/2013 | Ahiska |
| 2013/0021578 A1 | 1/2013 | Chen |
| 2013/0024819 A1 | 1/2013 | Rieffel |
| 2013/0030283 A1 | 1/2013 | Vortman et al. |
| 2013/0033640 A1 | 2/2013 | Lee |
| 2013/0033700 A1 | 2/2013 | Hallil |
| 2013/0035590 A1 | 2/2013 | Ma et al. |
| 2013/0035612 A1 | 2/2013 | Mason |
| 2013/0040720 A1 | 2/2013 | Cammegh |
| 2013/0041368 A1 | 2/2013 | Cunninghan |
| 2013/0049756 A1 | 2/2013 | Ernst et al. |
| 2013/0057702 A1 | 3/2013 | Chavan |
| 2013/0064426 A1 | 3/2013 | Watkins, Jr. |
| 2013/0064427 A1 | 3/2013 | Picard |
| 2013/0065517 A1 | 3/2013 | Svensson |
| 2013/0066448 A1 | 3/2013 | Alonso |
| 2013/0066526 A1 | 3/2013 | Mondragon |
| 2013/0069773 A1 | 3/2013 | Li |
| 2013/0070201 A1 | 3/2013 | Shahidi |
| 2013/0070257 A1 | 3/2013 | Wong |
| 2013/0072787 A1 | 3/2013 | Wallace et al. |
| 2013/0076863 A1 | 3/2013 | Rappel |
| 2013/0076944 A1 | 3/2013 | Kosaka |
| 2013/0077823 A1 | 3/2013 | Mestha |
| 2013/0079033 A1 | 3/2013 | Gupta |
| 2013/0084980 A1 | 4/2013 | Hammontree |
| 2013/0088584 A1 | 4/2013 | Malhas |
| 2013/0093866 A1 | 4/2013 | Ohlhues et al. |
| 2013/0096439 A1 | 4/2013 | Lee |
| 2013/0102879 A1 | 4/2013 | Maclaren et al. |
| 2013/0102893 A1 | 4/2013 | Vollmer |
| 2013/0108979 A1 | 5/2013 | Daon |
| 2013/0113791 A1 | 5/2013 | Isaacs et al. |
| 2013/0211421 A1 | 8/2013 | Abovitz et al. |
| 2013/0281818 A1 | 10/2013 | Vija et al. |
| 2014/0037174 A1 | 2/2014 | Ernst et al. |
| 2014/0073908 A1 | 3/2014 | Biber |
| 2014/0088410 A1 | 3/2014 | Wu |
| 2014/0148685 A1 | 5/2014 | Liu et al. |
| 2014/0159721 A1 | 6/2014 | Grodzki |
| 2014/0171784 A1 | 6/2014 | Ooi et al. |
| 2014/0205140 A1 | 7/2014 | Lovberg et al. |
| 2014/0378816 A1 | 12/2014 | Oh et al. |
| 2015/0085072 A1 | 3/2015 | Yan |
| 2015/0297120 A1* | 10/2015 | Son .................. A61B 5/721 |
| | | 600/410 |
| 2015/0331078 A1 | 11/2015 | Speck et al. |
| 2015/0359464 A1 | 12/2015 | Oleson |
| 2015/0366527 A1 | 12/2015 | Yu et al. |
| 2016/0035108 A1 | 2/2016 | Yu et al. |
| 2016/0073962 A1 | 3/2016 | Yu et al. |
| 2016/0091592 A1 | 3/2016 | Beall et al. |
| 2016/0166205 A1 | 6/2016 | Ernst et al. |
| 2016/0189372 A1 | 6/2016 | Lovberg et al. |
| 2016/0228005 A1 | 8/2016 | Bammer et al. |
| 2016/0249984 A1 | 9/2016 | Janssen |
| 2016/0256713 A1 | 9/2016 | Saunders et al. |
| 2016/0262663 A1 | 9/2016 | MacLaren et al. |
| 2016/0287080 A1 | 10/2016 | Olesen et al. |
| 2016/0310229 A1 | 10/2016 | Bammer et al. |
| 2016/0313432 A1 | 10/2016 | Feiweier et al. |
| 2017/0032538 A1 | 2/2017 | Ernst et al. |

FOREIGN PATENT DOCUMENTS

| | | |
|---|---|---|
| DE | 102004024470 | 12/2005 |
| EP | 0904733 | 3/1991 |
| EP | 1354564 | 10/2003 |
| EP | 1524626 A2 | 4/2005 |
| EP | 2515139 | 10/2012 |
| EP | 2948056 | 12/2015 |
| EP | 2950714 | 12/2015 |
| JP | 03023838 | 5/1991 |
| WO | WO 1996/017258 A2 | 6/1996 |
| WO | WO 99/38449 | 8/1999 |
| WO | WO 2000/072039 A1 | 11/2000 |

(56) References Cited

FOREIGN PATENT DOCUMENTS

| WO | WO 2003/003796 A1 | 1/2003 |
|---|---|---|
| WO | WO 2004/023783 A2 | 3/2004 |
| WO | WO 2005/077293 | 8/2005 |
| WO | WO 2007/025301 | 3/2007 |
| WO | WO 2007/085241 A1 | 8/2007 |
| WO | WO 2007/136745 | 11/2007 |
| WO | WO 2009/101566 | 8/2009 |
| WO | WO 2009/129457 A1 | 10/2009 |
| WO | WO 2011/047467 A1 | 4/2011 |
| WO | WO 2011/113441 A2 | 9/2011 |
| WO | WO 2012/046202 A1 | 4/2012 |
| WO | WO 2013/032933 A2 | 3/2013 |
| WO | WO 2014-005178 A1 | 1/2014 |
| WO | WO 2014/116868 | 7/2014 |
| WO | WO 2014/120734 | 8/2014 |
| WO | WO 2015/042138 | 3/2015 |
| WO | WO 2015/092593 | 6/2015 |
| WO | WO 2015/148391 | 10/2015 |
| WO | WO 2016/014718 | 1/2016 |

OTHER PUBLICATIONS

Maclaren et al., "Measurement and correction of microscopic head motion during magnetic resonance imaging of the brain", PLOS ONE, vol. 7(11):1-9 (2012).
International Search Report and Written Opinion received in International Patent Application No. PCT/US2015/022041 dated Jun. 29, 2015 in 9 pages.
Anishenko et al., "A Motion Correction System for Brain Tomography Based on Biologically Motivated Models." 7th IEEE International Conference on Cybernetic Intelligent Systems, dated Sep. 9, 2008, in 9 pages.
US 7,906,604, Mar. 2011, Lejeune et al. (withdrawn).
Armstrong et al., RGR-6D: Low-cost, high-accuracy measurement of 6-DOF Pose from a Single Image. Publication date unknown.
Armstrong et al., "RGR-3D: Simple, cheap detection of 6-DOF pose for tele-operation, and robot programming and calibration", In Proc. 2002 Int. Conf. on Robotics and Automation, IEEE, Washington (May 2002).
Fulton et al., "Correction for Head Movements in Positron Emission Tomography Using an Optical Motion-Tracking System", IEEE Transactions on Nuclear Science, vol. 49(1):116-123 (Feb. 2002).
Hoff et al., "Analysis of Head Pose Accuracy in Augmented Reality", IEEE Transactions on Visualization and Computer Graphics 6, No. 4 (Oct.-Dec. 2000): 319-334.
International Preliminary Report on Patentability for Application No. PCT/US2015/022041, dated Oct. 6, 2016, in 8 pages.
International Search Report and Written Opinion for Application No. PCT/US2015/041615, dated Oct. 29, 2015, in 13 pages.
Katsuki, et al., "Design of an Artificial Mark to Determine 3D Pose by Monocular Vision", 2003 IEEE International Conference on Robotics and Automation (Cat. No. 03CH37422), Sep. 14-19, 2003, pp. 995-1000 vol. 1.
Kiebel et al., "MRI and PET coregistration-a cross validation of statistical parametric mapping and automated image registration", Neuroimage 5(4):271-279 (1997).
Lerner, "Motion correction in fmri images", Technion-lsrael Institute of Technology, Faculty of Computer Science ( Feb. 2006).
Speck, et al., "Prospective real-time slice-by-slice Motion Correction for fMRI in Freely Moving Subjects", Magnetic Resonance Materials in Physics, Biology and Medicine., 19(2), 55-61, published May 9, 2006.
Yeo, et al. Motion correction in fMRI by mapping slice-to-volume with concurrent field-inhomogeneity correction:, International Conference on Medical Image Computing and Computer-Assisted Intervention, pp. 752-760 (2004).
Aksoy et al., "Hybrid Prospective and Retrospective Head Motion Correction to Mitigate Cross-Calibration Errors", NIH Publication, Nov. 2012.
Aksoy et al., "Real-Time Optical Motion Correction for Diffusion Tensor Imaging, Magnetic Resonance in Medicine" (Mar. 22, 2011) 66 366-378.
Andrews et al., "Prospective Motion Correction for Magnetic Resonance Spectroscopy Using Single Camera Retro-Grate Reflector Optical Tracking, Journal of Magnetic Resonance Imaging" (Feb. 2011) 33(2): 498-504.
Angeles et al., "The Online Solution of the Hand-Eye Problem", IEEE Transactions on Robotics and Automation, 16(6): 720-731 (Dec. 2000).
Bandettini, Peter A., et al., "Processing Strategies for Time-Course Data Sets in Functional MRI of the Human Breain", Magnetic Resonance in Medicine 30: 161-173 (1993).
Barmet et al, Spatiotemporal Magnetic Field Monitoring for MR, Magnetic Resonance in Medicine (Feb. 1, 2008) 60: 187-197.
Bartels, LW, et al., "Endovascular interventional magnetic resonance imaging", Physics in Medicine and Biology 48: R37-R64 (2003).
Carranza-Herrezuelo et al, "Motion estimation of tagged cardiac magnetric resonance images using variational techniques" Elsevier, Computerized Medical Imaging and Graphics 34 (2010), pp. 514-522.
Chou, Jack C. K., et al., "Finding the Position and Orientation of a Sensor on a Robot Manipulator Using Quaternions", The International Journal of Robotics Research, 10(3): 240-254 (Jun. 1991).
Cofaru et al "Improved Newton-Raphson digital image correlation method for full-field displacement and strain calculation," Department of Materials Science and Engineering, Ghent University St-Pietersnieuwstraat, Nov. 20, 2010.
Ernst et al., "A Novel Phase and Frequency Navigator for Proton Magnetic Resonance Spectroscopy Using Water-Suppression Cycling, Magnetic Resonance in Medicine" (Jan. 2011) 65(1): 13-7.
Eviatar et al., "Real time head motion correction for functional MRI", In: Proceedings of the International Society for Magnetic Resonance in Medicine (1999) 269.
Forbes, Kristen P. N., et al., "Propeller MRI: Clinical Testing of a Novel Technique for Quantification and Compensation of Head Motion", Journal of Magnetic Resonance Imaging 14: 215-222 (2001).
Glover, Gary H., et al., "Self-Navigated Spiral fMRI: Interleaved versus Single-shot", Magnetic Resonance in Medicine 39: 361-368 (1998).
Gumus et al., "Elimination of DWI signal dropouts using blipped gradients for dynamic restoration of gradient moment", ISMRM 20th Annual Meeting & Exhibition, May 7, 2012.
Herbst et al., "Preventing Signal Dropouts in DWI Using Continous Prospective Motion Correction", Proc. Intl. Soc. Mag. Reson. Med. 19 (May, 2011) 170.
Herbst et al., "Prospective Motion Correction With Continuous Gradient Updates in Diffusion Weighted Imaging, Magnetic Resonance in Medicine" (2012) 67:326-338.
Horn, Berthold K. P., "Closed-form solution of absolute orientation using unit quaternions", Journal of the Optical Society of America, vol. 4, p. 629-642 (Apr. 1987).
International Preliminary Report on Patentability for Application No. PCT/US2007/011899, dated Jun. 8, 2008, in 13 pages.
International Search Report and Written Opinion for Application No. PCT/US2007/011899, dated Nov. 14, 2007.
International Search Report and Written Opinion for Application No. PCT/US2014/012806, dated May 15, 2014, in 17 pages.
Josefsson et al. "A flexible high-precision video system for digital recording of motor acts through lightweight reflect markers", Computer Methods and Programs in Biomedicine, vol. 49:111-129 (1996).
Kiruluta et al., "Predictive Head Movement Tracking Using a Kalman Filter", IEEE Trans. on Systems, Man, and Cybernetics-Part B: Cybernetics, 27(2):326-331 (Apr. 1997).
Maclaren et al., "Combined Prospective and Retrospective Motion Correction to Relax Navigator Requirements", Magnetic Resonance in Medicine (Feb. 11, 2011) 65:1724-1732.
MacLaren et al., "Navigator Accuracy Requirements for Prospective Motion Correction", Magnetic Resonance in Medicine (Jan. 2010) 63(1): 162-70.

(56) References Cited

OTHER PUBLICATIONS

MacLaren, "Prospective Motion Correction in MRI Using Optical Tracking Tape", Book of Abstracts, ESMRMB (2009).
McVeigh et al., "Real-time, Interactive MRI for Cardiovascular Interventions", Academic Radiology, 12(9): 1121-1127 (2005).
Nehrke et al., "Prospective Correction of Affine Motion for Arbitrary MR Sequences on a Clinical Scanner", Magnetic Resonance in Medicine (Jun. 28, 2005) 54:1130-1138.
Norris et al., "Online motion correction for diffusion-weighted imaging using navigator echoes: application to RARE imaging without sensitivity loss", Magnetic Resonance in Medicine, vol. 45:729-733 (2001).
Ooi et al., "Prospective Real-Time Correction for Arbitrary Head Motion Using Active Markers", Magnetic Resonance in Medicine (Apr. 15, 2009) 62(4): 943-54.
Orchard et al., "MRI Reconstruction using real-time motion tracking: A simulation study", Signals, Systems and Computers, 42nd Annual Conference IEEE, Piscataway, NJ, USA (Oct. 26, 2008).
Park, Frank C. and Martin, Bryan J., "Robot Sensor Calibration: Solving AX-XB on the Euclidean Group", IEEE Transaction on Robotics and Automation, 10(5): 717-721 (Oct. 1994).
PCT Search Report from the International Searching Authority, dated Feburary 28, 2013, in 16 pages, regarding International Application No. PCT/US2012/052349.
Qin et al., "Prospective Head-Movement Correction for High-Resolution MRI Using an In-Bore Optical Tracking System", Magnetic Resonance in Medicine (Apr. 13, 2009) 62: 924-934.
Schulz et al., "First Embedded In-Bore System for Fast Optical Prospective Head Motion-Correction in MRI", Proceedings of the 28th Annual Scientific Meeting of the ESMRMB (Oct. 8, 2011) 369.
Shiu et al., "Calibration of Wrist-Mounted Robotic Sensors by Solving Homogeneous Transform Equations of the Form AX=XB", IEEE Transactions on Robotics and Automation, 5(1): 16-29 (Feb. 1989).
Tremblay et al., "Retrospective Coregistration of Functional Magnetic Resonance Imaging Data using External monitoring", Magnetic Resonance in Medicine 53:141-149 (2005).
Tsai et al., "A New Technique for Fully Autonomous and Efficient 3D Robotics Hand/Eye Calibration", IEEE Transaction on Robotics and Automation, 5(3): 345-358 (Jun. 1989).
Wang, Ching-Cheng, "Extrinsic Calibration of a Vision Sensor Mounted on a Robot", IEEE Transactions on Robotics and Automation, 8(2):161-175 (Apr. 1992).
Ward et al., "Prospective Multiaxial Motion Correction for fMRI", Magnetic Resonance in Medicine 43:459-469 (2000).
Welch at al., "Spherical Navigator Echoes for Full 3D Rigid Body Motion Measurement in MRI", Magnetic Resonance in Medicine 47:32-41 (2002).
Zaitsev, M., et al., "Prospective Real-Time Slice-by-Slice 3D Motion Correction for EPI Using an External Optical Motion Tracking System", Proc.Intl.Soc.Mag.Reson.Med.11:517(2004).
Zeitsev et al., "Magnetic resonance imaging of freely moving objects: Prospective real-time motion correction using an external optical motion tracking system", NeuroImage 31 (Jan. 29, 2006) 1038-1050.

\* cited by examiner

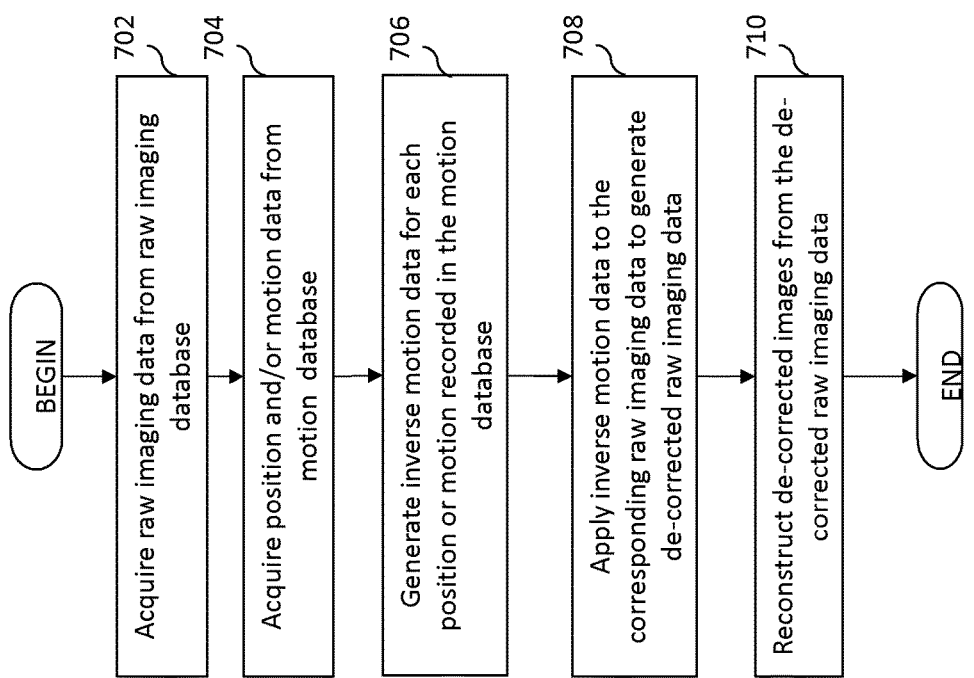

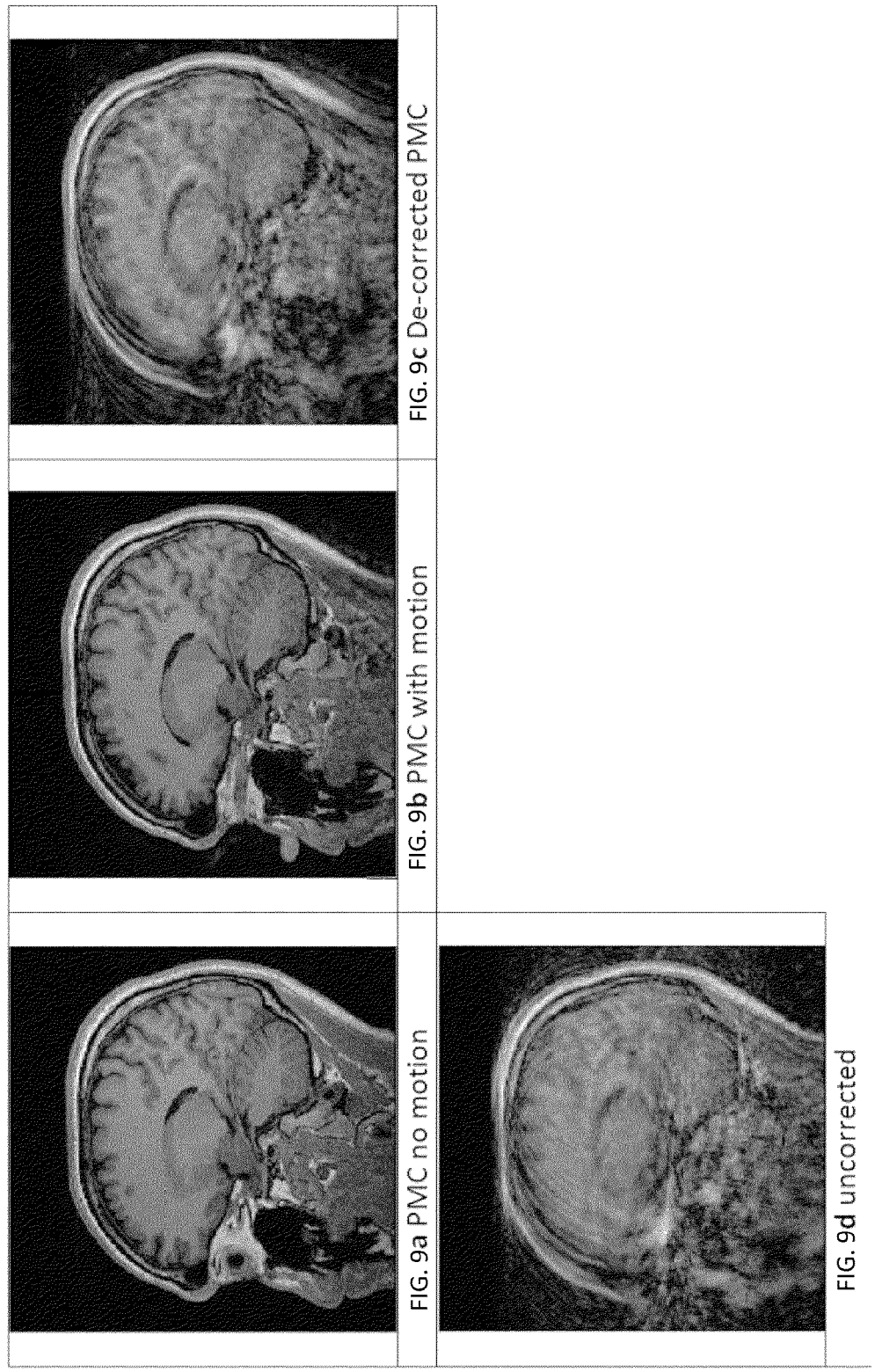

SYSTEMS, METHODS, AND DEVICES FOR REMOVING PROSPECTIVE MOTION CORRECTION FROM MEDICAL IMAGING SCANS

CROSS-REFERENCE TO RELATED APPLICATIONS

This application claims the benefit of U.S. Provisional Application No. 61/969,765, filed Mar. 24, 2014, and titled SYSTEMS, METHODS, AND DEVICES FOR REMOVING PROSPECTIVE MOTION CORRECTION FROM MEDICAL IMAGING SCANS, which is hereby incorporated herein by reference in its entirety.

STATEMENT REGARDING FEDERALLY SPONSORED R&D

This invention was made with government support under Grant Number R01-DA021146 awarded by the National Institutes of Health. The government has certain rights to this invention

BACKGROUND

Field

The disclosure relates generally to the field of medical imaging, and more specifically to systems, methods, and devices for removing prospective motion correction from medical imaging scans.

Description

Medical imaging scans are required for various medical treatments and/or diagnoses. Some medical imaging scan technologies require that a patient be scanned for an extended period of time, and any motion by the patient during this extended period of time can introduce motion artifacts and other errors into the resulting images. Accordingly, motion compensation techniques have been developed to compensate for patient motion during a scan. Although motion compensation techniques can in many instances improve clarity of images, among other benefits, such techniques are not without deficiencies.

SUMMARY

The disclosure herein provides systems, methods, and devices for removing prospective motion correction from medical imaging scans. For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

In certain embodiments, a system for generating motion de-corrected images in conjunction with a biomedical imaging scan comprises: a biomedical image scanner; one or more detectors configured to capture motion data for an object being scanned by the biomedical image scanner; a detector processing interface configured to generate motion tracking data from the captured motion data, the motion tracking data indicating the position of the object being scanned by the biomedical image scanner; a scanner controller configured to adjust the biomedical image scanner using the motion tracking data to compensate in real time for object motions, such that the raw image data generated by the scanner can be reconstructed into motion-corrected images; and an image processing interface comprising: a motion-corrected images generator configured to reconstruct images based on the raw image data generated by the scanner; and a motion de-corrected images generator configured to generate, based on the raw image data and the motion tracking data, de-corrected image data representative of what the scanner would produce had the scanner not compensated for motion, wherein the de-corrected image data can be reconstructed into de-corrected images.

In some embodiments, the motion de-corrected images generator generates de-corrected images by inverting the motion tracking data generated by the detector processing interface and applying the inverted motion tracking data to the raw image data to generate de-corrected image data. In some embodiments, the imaging processing interface is further configured to reconstruct images based on the de-corrected image data. In some embodiments, the image processing interface is further configured to: transmit motion-corrected images and the de-corrected images to an electronic display for simultaneous display to a user. In some embodiments, the motion-corrected images and the de-corrected images are displayed on an electronic display device. In some embodiments, the motion de-corrected images are generated using a regridding process to remove the effects of compensating for motions of the object being scanned. In some embodiments, the motion de-corrected images generator uses a SENSE algorithm to de-correct the raw image data using the motion tracking data. In some embodiments, the system further comprises a marker coupled to the object being scanned, wherein the detector processing interface is configured to track the motion of the marker to generate motion tracking data. In some embodiments, the detector processing interface further comprises a tracking combination component configured to combine two or more sets of tracking data to generate a position of the object being scanned. In some embodiments, the one or more detectors are at least partially embedded in a wall of the biomedical imaging scanner. In some embodiments, the biomedical imaging scanner comprises a wall positioned between an MRI magnet and a bore for positioning therein of a patient, the wall comprising a first side proximal to the bore and a second side distal to the bore, wherein the one or more detectors are positioned in a cavity adjacent the second side of the wall. In some embodiments, the scanner is one of an MRI or a CT scanning system.

In certain embodiments, a system for generating motion de-corrected images in conjunction with a biomedical imaging scan comprises: a magnetic resonance imaging (MRI) scanner; one or more detectors configured to capture motion data for an object being scanned by the MRI scanner; a detector processing interface configured to generate motion tracking data from the captured motion data, the motion tracking data indicating the position of the object being scanned by the MRI scanner; a scanner controller configured to adjust the MRI scanner using the motion tracking data to compensate in real time for object motions, such that the raw image data generated by the scanner can be reconstructed into motion-corrected images; and an image processing interface comprising: a motion-corrected images generator configured to reconstruct images based on the raw image data generated by the scanner; and a motion de-corrected images generator configured to generate, based on the raw image data and the motion tracking data, de-corrected image data representative of what the scanner would produce had the scanner not compensated for motion, wherein the de-corrected image data can be reconstructed into de-corrected images.

In certain embodiments, a computer implemented-method for generating motion de-corrected images in conjunction with a biomedical imaging scan comprises: tracking, by a computer system, motion of an object being scanned by a scanner; generating, by the computer system, motion tracking data indicating the position of the object being scanned; adjusting, by the computer system, a biomedical imaging scanner, using the motion tracking data, to compensate in real time for object motion, such that raw image data generated by the scanner can be reconstructed into motion-corrected images; inverting, by the computer system, the motion tracking data to generated inverted motion tracking data; and applying, by the computer system, the inverted motion tracking data to the raw image data to generate de-corrected image data representative of what the scanner would produce had the scanner not compensated for motion, wherein the de-corrected image data can be reconstructed into de-corrected images, wherein the computer system comprises an electronic memory and a computer processor.

In some embodiments, the computer-implemented method further comprises, reconstructing, by the computer system, images based on the de-corrected image data. In some embodiments, the computer-implemented method further comprises: reconstructing, by the computing system, images based on the raw image data generated by the scanner; and transmitting, by the computer system, the motion-corrected images and the de-corrected images to an electronic display for simultaneous display to a user. In some embodiments, the computer-implemented method further comprises: transmitting, by the computer system, data enabling display, simultaneously with the motion-corrected and de-corrected images, of a pictorial representation of the tracked motion. In some embodiments, tracking motion of an object being scanned comprises tracking motion of a marker coupled to the object. In some embodiments, tracking motion of an object being scanned comprises combining two or more sets of tracking data to generate a position of the object being scanned. In some embodiments, compensating in real time for object motion further comprises updating geometric parameters of the scanner based on an updated position of the object being scanned. In some embodiments, the scanner generates raw image data using a process comprising: exciting, by the biological image scanner, nuclei within the object being scanned; applying, by the biomedical image scanner, a magnetic field gradient across the object being scanned; and receiving, at a receiver coil, radiofrequency signals indicating one or more features of the object being scanned.

BRIEF DESCRIPTION OF THE DRAWINGS

The foregoing and other features, aspects, and advantages of the present invention are described in detail below with reference to the drawings of various embodiments, which are intended to illustrate and not to limit the invention. The drawings comprise the following figures in which:

FIG. 7 depicts an embodiment of a process flow diagram illustrating an example of removing motion correction from raw imaging data.

FIGS. 9A-9D depict various images from a medical imaging scan with and without motion correction.

DETAILED DESCRIPTION OF THE EMBODIMENTS

Figure 1:
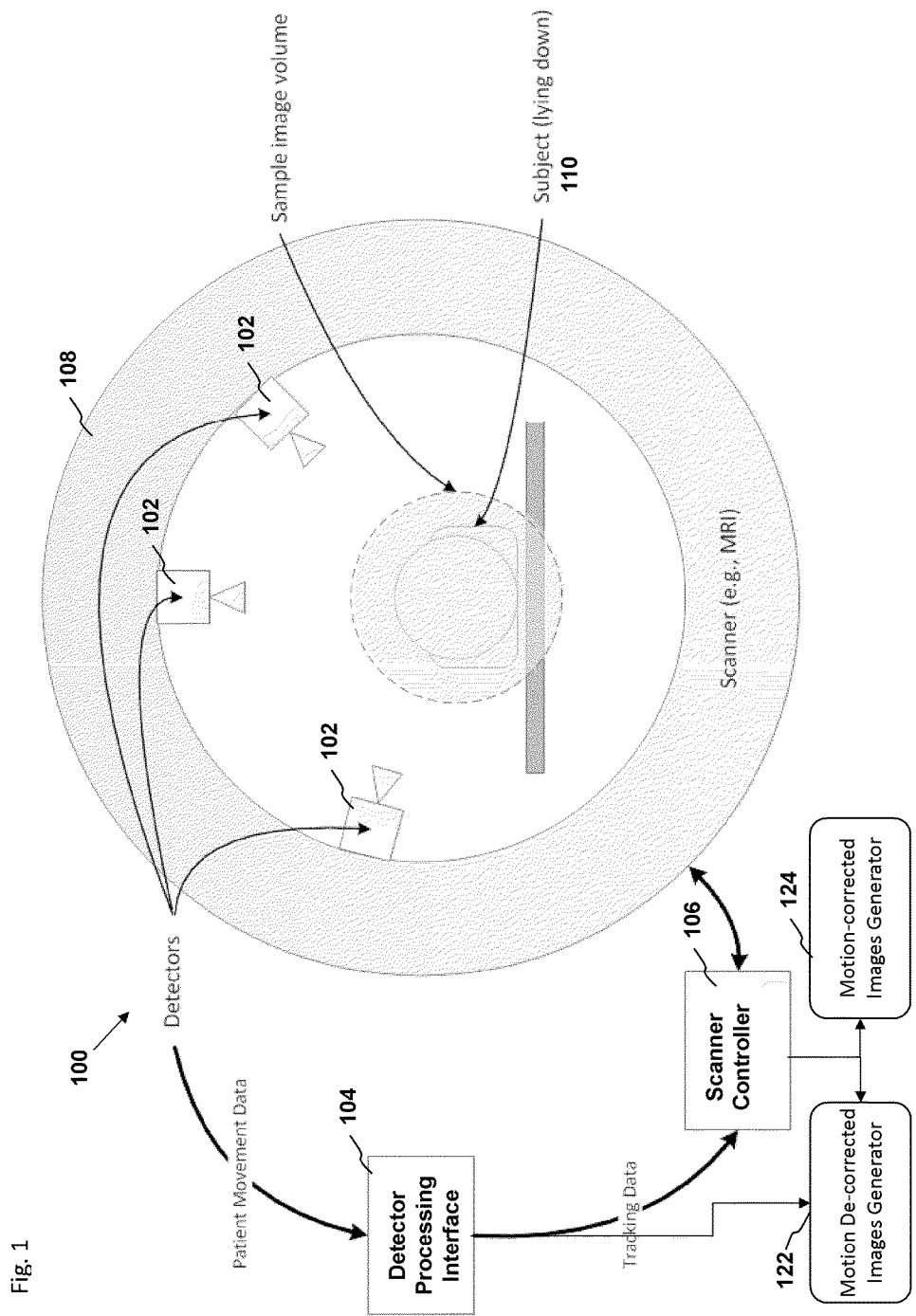
FIG. 1 depicts an embodiment of a schematic diagram illustrating a biomedical imaging motion compensation system.

The disclosure herein provides systems, methods, and devices for removing prospective motion correction from medical imaging scans. Medical imaging scans are required for various medical treatments and/or diagnoses. A variety of biomedical imaging scan technologies are available, such as magnetic resonance imaging (MRI), computed tomography (CT), and the like. Some medical imaging scan technologies require that a subject be scanned for an extended period of time. During a scan, any motion of the patient or object being scanned can introduce motion artifacts and other errors into the resulting images. For example, if a patient is having their brain scanned in an MRI machine, the resulting images may have motion artifacts and/or be blurry if the user or patient moves his or her head during scan. Motion compensation systems provide techniques for removing or preventing motion artifacts from showing up in a scan.

Although motion compensation systems can be beneficial in removing motion artifacts from medical imaging scans, some deficiencies in motion tracking and compensation systems exist. Because of potential deficiencies in compensation systems, some users of a medical imaging scanner, such as an MRI scanner operator, may not trust that the motion-compensated images are better than what would have been produced without motion compensation. Further, in some instances, such as, for example, when a patient did not move at all during a scan, a motion-compensated image may actually be of worse quality than if motion correction had not been applied. Accordingly, it can be beneficial to generate two or more sets of image data, some sets being motion-corrected, and other sets not being motion-corrected, so that a user can view the two or more sets of data to determine which is better to use and/or to instill a level of comfort that the motion-corrected data is better than the non-motion corrected data.

Further, many medical devices require clearance from the FDA. In achieving such clearance, the applicant may be required to show that a system works as intended. Accordingly, to achieve clearance for a motion compensation system, it can be useful to be able to generate both motion-corrected images and non-motion corrected images to show that the motion-corrected data is better or at least within requirements of the FDA.

Prospective motion correction can enable a medical imaging scanner to adjust itself in real time in response to tracking of patient motion. Prospective motion correction can thus enable images to be as accurate as possible. However, if prospective motion correction is applied, meaning the source data created by the scanner has already been compensated for motion, a problem arises in being able to provide non-motion corrected data. In such a case, non-motion corrected data was never acquired by the scanner; thus, if non-motion corrected data is to be presented to a user, in some embodiments it can be derived from the motion corrected data.

Various technologies have been developed to enable compensation for subject motion during a scan. For example, in some embodiments, a motion compensation system is configured to track movement or motion of an object being scanned and to adjust the scanner in real time to compensate for that motion. Examples of such technology may be found in U.S. Pat. No. 8,121,361, entitled MOTION TRACKING SYSTEM FOR REAL TIME ADAPTIVE IMAGING AND SPECTROSCOPY, filed on May 18, 2007 ('361 Patent), Patent Cooperation Treaty Application No. PCT/US2014/013546, entitled MOTION TRACKING SYSTEM FOR REAL TIME ADAPTIVE MOTION COMPENSATION IN BIOMEDICAL IMAGING, filed on Jan. 29, 2014 ('546 Application), U.S. patent application Ser. No. 13/594,563, entitled METHODS, SYSTEMS, AND DEVICES FOR INTRA-SCAN MOTION CORRECTION, filed on Aug. 24, 2012 ('563 Application), and Patent Cooperation Treaty Application No. PCT/US2014/012806, entitled SYSTEMS, DEVICES, AND METHODS FOR TRACKING AND COMPENSATING FOR PATIENT MOTION DURING A MEDICAL IMAGING SCAN, filed on Jan. 23, 2014 ('806 Application). Each of the forgoing patents and applications is hereby incorporated by reference herein in its entirety. In some embodiments, motion compensation can be in real time, meaning the raw image data outputted from a scanner has already been compensated for motion. This is sometimes termed prospective motion correction (PMC). For example, the system may record the orientation of the subject while performing the scan and store the raw imaging data according to the orientation of the subject and scanner. In other embodiments, motion compensation can be after the fact, such as by converting raw non-compensated scanner data into motion-compensated data through post-processing of the raw scanner data in conjunction with motion tracking data. In some embodiments described herein, a motion correction removal system is configured to remove motion compensation from data generated as part of a prospective motion correction system. However, in some embodiments, similar concepts may also be applied to a post-processing system.

One potential option for creating non-motion corrected data and motion corrected data for comparison is to run a first scan with the motion correction and a second scan without motion correction. For example, a second scan may be performed while a patient is instructed to remain as still as possible to compare with motion corrected images of the same or a different patient. Alternatively, the second scan may utilize a phantom object instead of a patient. During the second scan, the tracked motion data from the first scan can be used to simulate the motion of the patient in the first scan. This can therefore introduce motion artifacts into the second scan similar to what would have occurred in the first scan if PMC had not been used during the first scan. Such a process has deficiencies. For example, the resulting images from the second scan will not be of the same scan as the first scan. Further, this process requires that the patient in the second scan remain as still as possible. If the patient moves, even through involuntary movements such as breathing, twitching, or other movement, the non-motion corrected data will be flawed. Another deficiency is that the patient may be required to undergo two scans, exposing the patient to further, for example, MRI emissions, extending the time required to conduct an MRI scan, and reducing the overall quality of treatment.

Unlike the two-scan process described above, embodiments of systems, methods, and devices disclosed herein enable both motion-corrected and non-motion corrected imaging data to be created from a single imaging scan. This reduces the number of scans that must be performed increasing the efficiency of the process. Accordingly, the system is configured to enable faster acquisition, processing, and displaying of both motion corrected and motion de-corrected images from a biomedical imaging scan. In addition, the reduced number of scans exposes a subject to reduced radiation. In some embodiments, the non-motion corrected data is referred to as de-corrected imaging data. For example, a system can be configured to acquire motion-compensated imaging data using prospective motion compensation, and to then de-correct that imaging data utilizing the tracked motion of the patient to provide a second de-corrected motion set that simulates what the scan would have produced had prospective motion correction not been used.

The de-correction process may start with raw imaging data from a scanner, which was acquired using prospective motion correction. The raw imaging data may include (or otherwise be associated with) tracking or motion data indicating the position and/or movement of the subject during the scanning process. To de-correct the raw imaging data, the system may invert the position and/or motion data of the user. The inverted motions can then be applied to the raw imaging data to generate a set of de-corrected raw imaging data. The de-corrected raw imaging data can then be reconstructed into de-corrected images for review by a user and comparison to motion-corrected images reconstructed from the original raw imaging data.

Although several embodiments, examples, and illustrations are disclosed, it will be understood by those of ordinary skill in the art that the inventions described herein extends beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

The embodiments and examples described herein are generally discussed in the context of patient scanning, in particular with an MRI scanner. However, the scope of the disclosure is not limited to scanning with an MRI, medical imaging scanning, or otherwise. The system may incorporate a variety of scanning systems or types in addition to, or instead of, an MRI scanner. Additionally, while the example embodiments are discussed in the context of a human patient, a scanning system incorporating the features disclosed herein may be used to scan humans, animals, plants, inanimate objects, and/or the like.

The embodiment of a motion compensation system 100 illustrated in FIG. 1 is not shown to scale, but is rather shown at a scale that helps facilitate illustration of the system. Other figures are also not shown to scale. Additionally, most embodiments illustrated in these figures and described in this specification comprise a motion compensation system operating in real time or substantially in real time to correct a scanner for motion of a patient or object. However, in other embodiments, a motion compensation system can be configured to operate by processing images using post-processing after they have been created by a scanner to remove any motion artifacts.

Motion De-Correction Systems

FIG. 1 is an embodiment of a schematic diagram illustrating a motion tracking system 100. The motion tracking system 100 comprises one or more detectors 102, a detector processing interface 104, a scanner controller 106, and a scanner 108. In an embodiment, the one or more detectors 102 are positioned generally within an interior volume of the scanner 108 (one of ordinary skill in the art will appreciate that the one or more detectors can be positioned in other locations, for example, outside the volume of the scanner, embedded at least partially in a wall or magnet of the scanner, and/or the like) and positioned to each have a different viewpoint from which to view the subject 110 or to detect information describing at least one feature or quality of the subject 110. For example, features or qualities of the subject 110 that may be detected by various detectors 102 include but are not limited to a visual image or depiction of the subject 110 or a portion of the subject 110, a distance of the subject 110 or a portion of the subject 110 to the detector 102, a surface texture of the subject 110 or a portion of the subject 110, an indentation or protrusion of the subject, an opening or orifice of the subject, a structural outline of the subject or a portion of the subject, another anatomical landmark or feature of the subject, or a marker attached to the subject. Various embodiments may be configured to employ various numbers of detectors 102 (including a single detector, two detectors, three detectors, or more detectors), and the detectors 102 can be positioned places other than within an interior volume of a scanner, as long at the detectors 102 are positioned to enable viewing the subject 110 or detecting information describing at least one quality of the subject 110 (for example, "patient movement data").

During an imaging scan, the detectors 102 are configured to acquire patient movement data and send the data to the detector processing interface 104. The detector processing interface 104 is configured to analyze the patient movement data using one or more tracking controllers or filters and to create tracking data describing movement or motion of the patient/object of interest in detector and/or scanner reference or coordinate frames. The tracking data is sent from the detector processing interface 104 to the scanner controller 106, the motion de-corrected images generator 122, and the motion corrected images generator 124. The scanner controller 106 is configured to adjust the scanner 108 in real time based on patient/object of interest movement described in the tracking data to enable creation of scanned images with no or few motion artifacts. For example, the scanner controller 106 can be configured to adjust scan planes, locations, and/or orientations of the scanner 108 in real time.

In some embodiments, the tracking data generated by the detector processing interface 104 is used to compensate for motion during image reconstruction or post-processing, rather than to directly adjust the scanner 108. In some embodiments, tracking data is used to both compensate for motion during image reconstruction and to directly adjust the scanner 108.

The motion de-corrected images generator 122 receives raw imaging data from the scanning controller 106 and movement data from the detector processing interface 104. The de-corrected images generator then uses the motion data to generate images as they would have been without motion compensation. For example, in some embodiments, the motion data may indicate a position of a patient's head, which the scanner controller 106 used to adjust the scanner 108 to capture data in the correct orientation while scanning. The de-corrected images generator 122 may then use the motion data to adjust the raw imaging data to the orientation the scanner would have seen if not for the compensation. The de-corrected images generator 122 then generates images based on the adjusted raw imaging data. The motion-corrected images generator 124 uses the raw imaging data to generate motion compensated images. In some embodiments, the motion data is used by the motion-corrected images generator 124 in a post-processing technique to compensate the raw imaging data based on a record of the patient's movement. In such embodiments, the de-corrected images generator may not use the motion data, but instead generate images based directly on the raw imaging data from the scan that taken while not compensating for motion.

The term "detector" as used herein is a broad term, and unless otherwise indicated the term can include within its meaning, without limitation, a camera (either digital or analog, and either capable of capturing still images or movies) that can detect the visible spectrum or other portions of the electromagnetic spectrum, a proximity sensor, an ultrasonic sensor, a radar sensor, a laser-based sensors, time-of-flight cameras, or any other kind of detector. In embodiments where the detector is positioned within the bore of a medical imaging device, the term "detector" includes within its meaning a detector that is configured to not interfere or only comprises components that do not interfere with the imaging capability of the medical imaging device, for example, the detector does not generate electrical or magnetic interference that could cause artifacts in the images generated by the medical imaging device. In some embodiments one or more of the detectors may be fully or partially disposed within the wall of a scanner. For example, the detectors may be located in a cavity of scanning system. For example, an MRI scanner may comprise a cylindrical magnet that is positioned around a bore for positioning therein of a patient. In some embodiments, one or more detectors or cameras may be positioned at least partially within such magnet. In some embodiments, the magnet is at least partially positioned within a cavity of a housing. In some embodiments, the one or more detectors may be positioned at least partially within that housing. In some embodiments, the housing comprises a wall that separates the bore for positioning therein of the patient from the magnet. In some embodiments, the one or more detectors may be positioned in, on, or adjacent to such wall. In some embodiments, the detectors may be positioned adjacent to a surface of the wall that is distal to the patient bore. In some embodiments, the detectors are positioned within a cavity at least partially defined by the wall, the detectors are configured to view the patient bore area through a hole or other at least partially transparent portion of the wall.

Various embodiments of motion tracking systems can be configured to use various types of detectors. In some embodiments, the detectors 102 are all cameras, with each detector 102 being configured to continuously record a partial or full view of the object of interest, such as a subject's face in the case of tracking a patient's head. Recording the partial or full views from various detector vantage points can enable increased accuracy and/or redundancy of various tracking techniques. In some embodiments, the detectors 102 may be cameras, laser-based sensors, projection-based sensors, radar sensors, ultrasonic sensors, other remote sensors, or any combination thereof.

The various components illustrated in FIG. 1 may be integrated into a biomedical scanning system or may be an add-on feature. For example, each of the components may be built directly into a scanning system during original manufacture. In some other embodiments, the components may be added onto an existing biomedical scanning system. For example, the detectors may be installed into a cavity within the biomedical scanner separately. In addition, in some embodiments, the processing is performed by the already existing computer systems specific to a biomedical scanning system. However, in some embodiments, additional computing system may be installed to perform the motion de-correction processes described herein.

Figure 2:
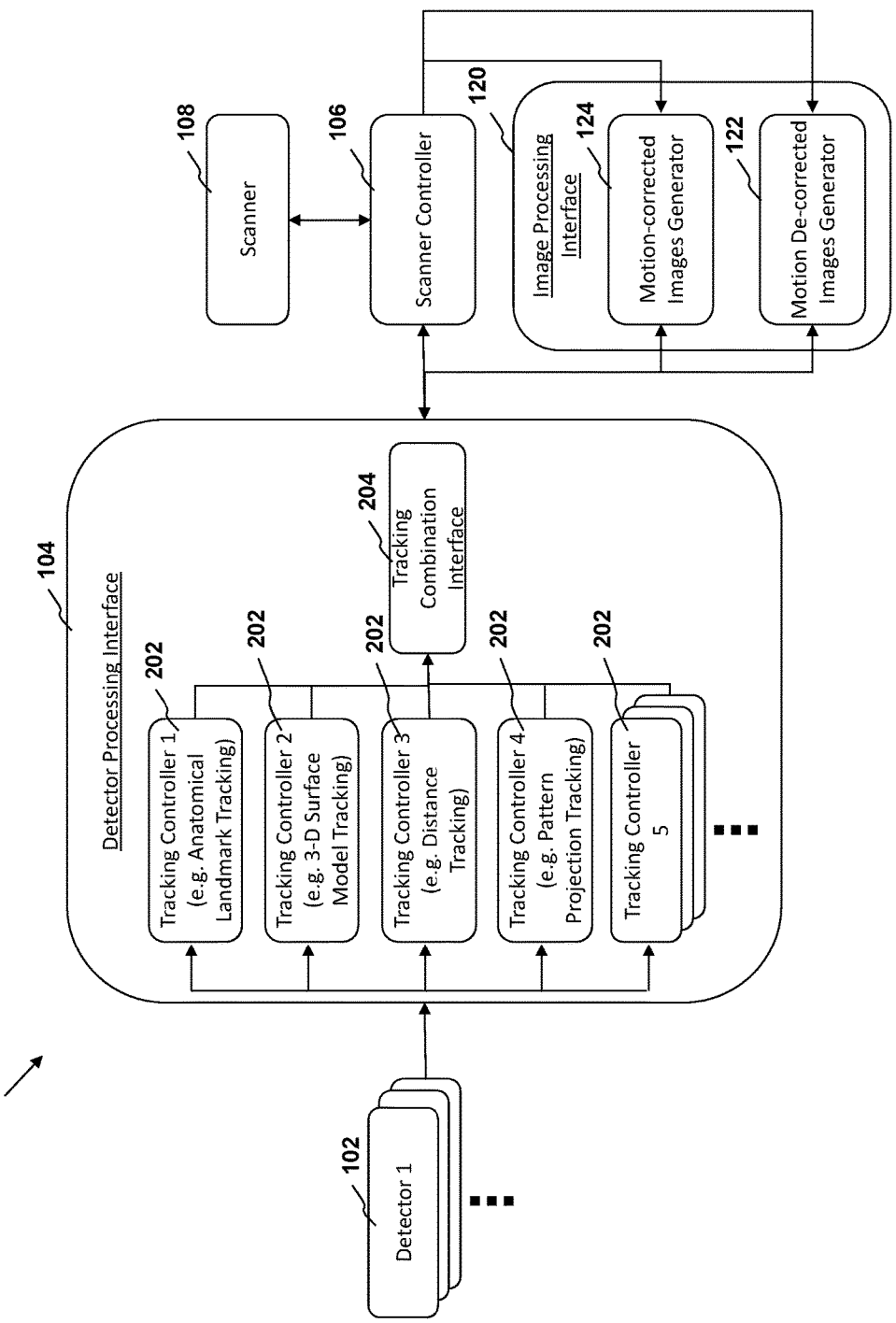
FIG. 2 is a block diagram depicting another embodiment of a biomedical imaging motion compensation system.

FIG. 2 is a block diagram depicting an embodiment of a motion tracking system 200. The motion tracking system 200 comprises one or more detectors 102, a detector processing interface 104, a scanner controller 106, and a scanner 108, and an image processing interface 120. The detector processing interface further comprises several tracking controllers or filters 202 and a tracking combination interface 204. In the motion tracking system 200, the one or more detectors 102 send patient movement data (for example, camera images, distance estimates, signals, or the like) to the detector processing interface 104, and each of the several tracking controllers or filters 202 uses the patient movement data (or a portion of the patient movement data) to generate an estimate of movement of the patient/object of interest (for example, describing all six degrees of freedom or fewer than six degrees of freedom). The tracking combination interface 204 is configured to receive each tracking controller's individual estimate and to combine them (or to select one of them) to create tracking data comprising a single or unitary movement estimate to send to the scanner controller 106. The tracking combination interface 204 may also be configured to send no motion updates to the scanner controller 106, for example, to retain the most recent motion data, if the difference in motion or amount or magnitude of tracked motion does not exceed a predetermined threshold. The scanner controller 106 is configured to update one or more parameters of the scanner 108 in real time based on this tracking data received from the detector processing interface 104. The image processing interface 120 further comprises a motion-corrected images generator 124 and a motion de-corrected images generator 122, which generate two sets of images, one with motion compensation and one with non-motion compensated images.

Several possible tracking controllers or filters 202, as shown in FIG. 2, either in isolation or in combination, can be configured to track the object of interest. One embodiment of a tracking controller or filter 202, for example Tracking Controller 1 shown in FIG. 2, is configured to track the position and orientation of anatomical features or "landmarks" during subject movement, and uses this information to derive the object of interest's (for example, the subject's head) movement. For example, when tracking a subject's head, if the position of the subject's two eyes and the position of the tip of the subject's nose are known in detector coordinates, then the three translations and three rotations of the subject's head can be derived by means of triangulation or other methods. In general, accuracy of such a tracking controller or filter 202 can be improved by tracking a greater number of anatomical features. For example, if the position of a subject's nostrils and/or the bridge of the nose are tracked in addition to the nose tip and the eyes, then tracking of the subject's head can be generally more accurate. Tracking accuracy can also be improved by utilizing a greater number of detectors 102 and/or positioning the detectors 102 to view the subject's head from a variety of angles. Furthermore, in some embodiments, a single tracking controller or filter can be configured to provide data for less than all six degrees of freedom, i.e. less than three translations and three rotations, in which case information from one or more other tracking controllers or filters may be used to complete the tracking of all six degrees of freedom.

Another embodiment of a tracking controller or filter 202, for example Tracking Controller 2 shown in FIG. 2, is configured to create a three-dimensional surface model of the object of interest (for example, a subject's head), and to calculate motion tracking information based on changes to the three-dimensional surface model as it is updated when the subject moves. A three-dimensional surface model tracking controller or filter can be configured to employ various types of detectors 102 and modeling methods. For example, the controller or filter is configured to create a surface model based on a surface texture of the object as detected by a detector or as detected by the scanner. In an embodiment, the controller or filter is configured to create a surface model based on changes in lighting and/or shading of the object of interest.

Some embodiments of tracking controllers or filters 202, for example Tracking Controller 3 shown in FIG. 2, are configured to use estimates of a distance of the object of interest (or a portion or portions of the object of interest) to one or more of the detectors 102. The position of the object of interest can then be estimated or derived by combining the distance estimates from multiple detectors 102 and/or by monitoring changes in the distance estimates from an individual detector 102. Some distance estimation controller embodiments are configured to utilize, for example, range imaging, stereo triangulation, interferometry, or the like.

Other embodiments of tracking controllers or filters 202, for example Tracking Controller 4 shown in FIG. 2, are configured to track changes in a known pattern, for example, a regular grid, projected onto the object of interest. A projector projects one or more patterns onto the object of interest from one or more projection locations, and one or more detectors 102 detect images of the pattern projected onto the object of interest. The tracking controller or filter 202 is configured to analyze deformations and/or changes to the projection(s) as the subject 110 moves to derive an estimate of the object of interest's positioning.

Some embodiments of tracking controllers or filters 202 are configured to track light reflected from reflective and/or absorbent particles suspended or contained in a compound applied to a subject's skin. The compound can be, for example, a paste, a cream, a glue, a temporary tattoo, an ink, and the like. The compound can be painted, smeared, drawn, brushed, or otherwise applied to the subject's skin. The reflective particles can be configured to reflect light in different directions as the subject moves or rotates the skin area having the compound applied. For example, the reflective particles can be prisms that refract light in a known fashion, glitter particles, or the like. The absorbent particles can also be configured to absorb light in different directions as the subject moves or rotates the skin area having the compound applied. For example, the absorbent particles can be dark spheres that absorb light in a known fashion, or the like. This embodiment of a tracking controller or filter 202 is configured to analyze images detected by the detectors 102 to track light reflections and/or alterations from the various reflective and/or absorbent particles in order to determine movement of the object of interest. In some embodiments, the tracking controller or filter 202 is configured to track reflections and/or absorption of ambient light. In some embodiments, the tracking controller or filter 202 is configured to track reflections and/or absorptions of an auxiliary light source directed generally toward the reflective and/or absorbent particles.

In some embodiments, various embodiments of tracking controllers or filters 202 (including those described above and those using various other techniques) can be used either independently or in combination with other tracking controllers or filters, including markerless tracking controllers or filters, and modules utilizing markers for motion tracking (for example, markers placed on the subject or object being scanned, markers held by the object or subject being scanned, and/or the like). A tracking combination interface, such as the tracking combination interface 204 shown in FIG. 2, can be configured to receive position or movement estimates from a variety of tracking controllers or filters 202 and to either select one of the estimates to send to the scanner controller 106 or to combine one or more of the estimates to form a single or unitary, more accurate estimate to send to the scanner controller 106. In some embodiments, the position or movement estimates received by the tracking combination interface 204 each describe six degrees of freedom (for example, three translations and three rotations). In some embodiments, the position or movement estimates received by the tracking combination interface 204 each describe fewer than six degrees of freedom. In some embodiments, some of the position or movement estimates received by the tracking combination interface describe six degrees of freedom, while others describe fewer than six degrees of freedom. Tracking combination interface 204 can be configured to combine estimates from tracking controllers or filters 202. In some embodiments, a tracking combination interface can be configured to send no motion updates to the scanner controller if the difference in motion or an amount or magnitude of tracked motion does not exceed a predetermined threshold. In some embodiments, only a single tracking technique is utilized, and no tracking combination interface is used.

In some embodiments, all or some of the tracking controllers or filters 202 can be configured to use the same technique, but with different configurations. For example, a detector processing interface 104 can comprise multiple tracking controllers or filters 202 utilizing anatomical landmark tracking, with each tracking controller or filter 202 being configured to track a different anatomical landmark or set of anatomical landmarks. Additionally, in some embodiments, tracking controllers or filters 202 can be configured to utilize more than one tracking technique. For example, a tracking module 202 can be configured to utilize both anatomical landmark tracking and three-dimensional surface model tracking, but to send one unitary tracking estimate based on a combination of both methods to the tracking combination interface 204 for combination with the estimates of other tracking controllers or filters 202.

The motion de-corrected images generator 122 can in some embodiments be configured to use the motion data generated by the tracking combination interface 204 to de-correct the raw imaging data provided by the scanner 108 during the scanning process. The motion data may, for example, indicate a position of the patient or a movement of the patient since the last set of data was taken by the scanner 108. For example, the raw imaging data generated by the scanner may comprise (or otherwise be associated with) a set of data including position or location data corresponding to specific readings for the scanner. For example, the data may include scan planes, locations, or orientations of the scanner. The motion data may then indicate the position of the patient when a specific scan was taken by the scanner. In order to de-correct the raw imaging data, the de-corrected images generator 122 may be configured to, in some embodiments, adjust the orientation, location, and/or other parameter (or simulate such adjustment) associated with a reading to the position or configuration it would have been in if not for prospective motion compensation. The motion de-corrected images generator 122 may then generate images from the de-corrected raw imaging data. The motion-corrected images generator 124 generates images based on the raw imaging data. The images generated by both the de-corrected images generator 122 and the motion-corrected images generator 124 may be electronically stored for later review or one or both sets of images may be presented on a display screen. Example processes of generating de-corrected images are discussed further below with reference to FIGS. 3-9.

Motion De-Correction Processes

Figure 3:
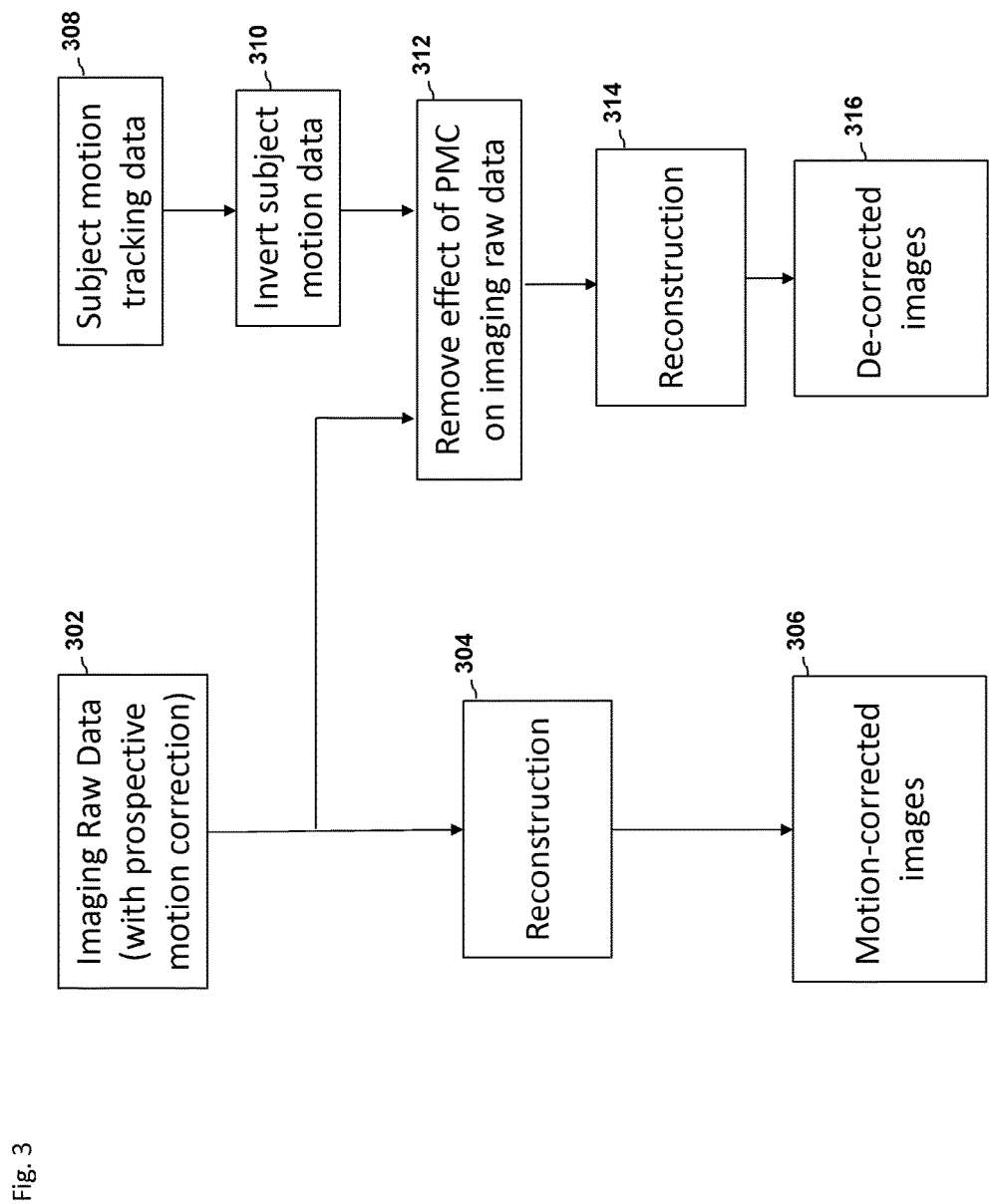
FIG. 3 depicts an embodiment of a process flow diagram illustrating an example of a motion correction removal process.

FIG. 3 illustrates an embodiment of a process flow diagram depicting a process for generating both motion corrected and de-corrected images from a single medical imaging scan. At block 302, raw imaging data is provided by a scanner controller, such as the scanner controller 106. In this embodiment, the raw imaging data provided by the scanner controller has been corrected for patient motion using prospective motion correction. At block 304, the raw imaging data is reconstructed by, for example, the motion-corrected images generator 124 to produce motion-corrected images 306 for viewing by, for example, a radiologist.

At block 308, subject motion tracking data is provided. For example, the detector processing interface 104 can be configured to provide object orientation tracking data to the motion de-corrected images generator 122. In some embodiments, the motion tracking data is provided with and/or embedded in the raw imaging data. In some embodiments, the motion tracking data is associated with and or correlated with the raw imaging data, enabling the system to determine how specific portions of the motion tracking data correspond to specific portions of the raw imaging data. At block 310, the motion de-corrected images generator can be configured to invert the motion tracking data. For example, the motion tracking data may indicate that a patient rotated his or her head to the left. The system can be configured to invert this information such that the data for use in removing motion correction would indicate that the motion is to the right instead of to the left. For clarity, this is a relatively simple example, but one of skill in the art will recognize that inverting the data may be a relatively complex mathematical operation, involving in some embodiments inversion of data describing motion, orientation, or pose in, for example, six degrees of freedom. In some embodiments, block 310 is not used and the effects of motion compensation are removed directly using the motion data.

At block 312, the inverted motion data is utilized to remove the effects of prospective motion correction from the raw imaging data. For example, the motion de-corrected images generator 122 can be configured to utilize regridding or other processes or algorithms to remove the effects of prospective motion correction from the imaging raw data prior to image reconstruction. Gridding is a method of interpolating data from an arbitrary sampling pattern to a uniform grid. The results of block 312 in some embodiments is raw imaging data similar to the raw imaging data provided at block 302, but created as if prospective motion correction had not been utilized during scan. At block 314, the system can be configured to reconstruct the raw imaging data with PMC removed to generate de-corrected images. The reconstruction process in block 314 may be the same or similar to as is used in block 304. For example, the de-corrected raw imaging data may be in the same format as the raw imaging data and may be compatible for reconstruction by the same system. At block 316, the de-corrected images are provided. In some embodiments, the system can be configured to display the de-corrected images next to the motion corrected images so that a user can compare the two to see which image is better and/or to prove that the motion corrected images are better.

Figure 4:
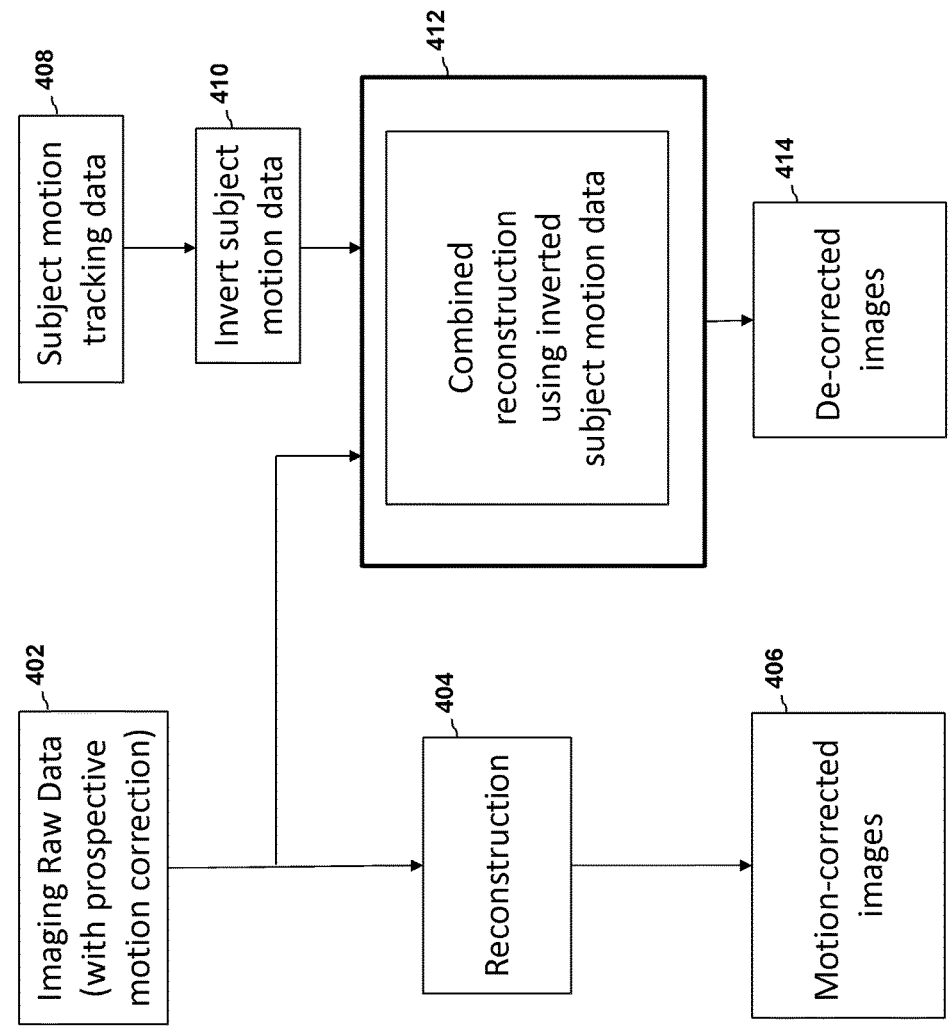
FIG. 4 depicts another embodiment of a process flow diagram illustrating an example of a motion correction removal process.

FIG. 4 illustrates another embodiment of a process flow depicting a motion de-correcting process. In this example, the process is similar to the process flow illustrated in FIG. 3. However, unlike in FIG. 3, the imaging data is received using a parallel imaging technique. For example, the scanner may generate raw imaging data with spatial encoding based on sampling in parallel from an array of RF coils. In this case, based on the algorithm being used to generate the raw imaging data, the effect of the prospective motion correction is removed during the reconstruction from the raw imaging data. At block 402, raw imaging data generated with prospective motion correction applied is provided, for example by scanner controller 106. At block 404, the system is configured to reconstruct the raw imaging data into motion-corrected images, which are provided at block 406. At block 408, subject motion tracking data is provided. At block 410, the subject motion tracking data is inverted to be used in de-correcting the raw image data.

At block 412, the imaging raw data is de-corrected and reconstructed into de-corrected images using the inverted subject motion data. For example, the motion de-corrected images generator 122 can be configured to utilize the SENSE technique or algorithm with the inverted subject motion data to generate de-corrected images and/or de-corrected imaging raw data. SENSE is a parallel imaging reconstruction technique utilized in magnetic resonance imaging. Although in this embodiment the SENSE technique or algorithm is used, various other processes or algorithms could be used in de-correcting raw image data using subject motion tracking data or inverted subject motion tracking data. For example, the system may be configured to use SENSE, SMASH, GRAPPA, AUTO-SMASH, compressed sensing, and/or the like. Further these or similar techniques may be used as applied to imaging technologies other than MRI. At block 414, the de-corrected images are provided.

Figure 5A:
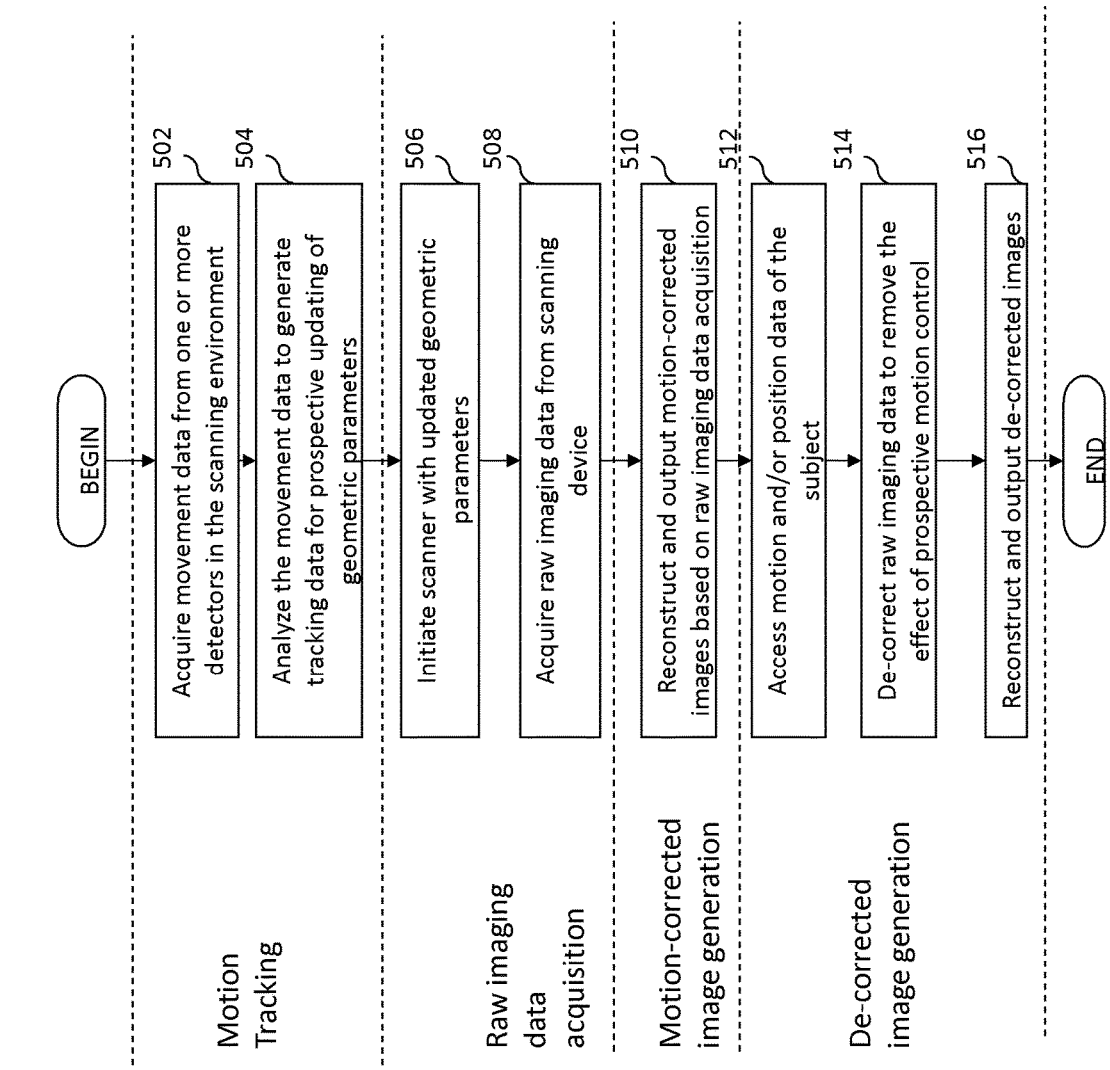
FIGS. 5A and 5B depict additional embodiments of a process flow diagram illustrating examples of motion correction removal processes.

FIG. 5A illustrates a process flow of an example of embodiments of one or more methods of de-correcting image data generated using prospective motion control. Beginning in block 502, the system acquires movement data from a plurality of detectors (or in some embodiments, one or more detectors) in the scanning environment. In block 504, the system analyzes the movement data to generate tracking data for prospective updating of geometric parameters (and/or other parameters) for use when acquiring scanning data. The tracking data may include a position or pose of the subject in comparison to a baseline position, motion of the subject in comparison to a previous position of the subject, and/or the like. The position and/or motion data generated by the system is also, in some embodiments, stored in a database for access later when generating de-corrected images. For example, the detector processing interface 104 may generate motion or position data of a subject using one or more tracking controllers 202 and a tracking combination interface 204 as discussed above. The prospective updates may be used by the scanner controller 106 in real time to direct the slices of imaging data taken by the scanner 108. In some embodiments, the geometric updates are made immediately prior to radiofrequency pulses are applied in order to accurately determine the position of readings that are taken by the scanner. By updating the geometry parameters and/or slice planes immediately prior to all radiofrequency pulses, a line-by-line correction of motion between successive excitations is possible. In other words, signals throughout the entire measurement can be aligned in position.

Moving on to block 506 and 508 the scanner performs raw imaging data acquisition. In block 506 the system initiates the scanner in preparation to take a set of scans. For example, in an MRI scanning system, the scanner may apply an RF pulse to excite nuclei in the subject. Then in block 508 the scanning device acquires raw imaging data at one or more receivers. The raw imaging data is acquired with compensation for any motion by the subject during the scanning process. Thus, in block 510, the images can be reconstructed directly from the raw imaging data acquired in block 508 to generate motion corrected images. The process used in block 510 may be one based on traditional imaging technologies or based on parallel processing techniques.

In block 512, the system accesses the motion or position data of the subject corresponding to the scanning process. For example, the position of the subject used to generate geometric updates for use by the scanner may be stored in a matrix with position data corresponding to the data acquired by the scanner at the same time. The position and/or motion data may indicate the position of the subject in up to six degrees of freedom. The corresponding image data may be stored correlated with the motion or position or tracking data that was used to adjust the scanner during data acquisition.

In block 514, the system de-corrects the raw imaging data to remove the effect of the prospective motion control. In some embodiments, the system may de-correct the data, by inverting the positions and/or motions of the subject during the scanning process. For example, if the position of the subject during one step of scanning indicates that the subject was rotated 5 degrees to the left, the system may invert the position to rotate the position of the data 5 degrees to the right. Similar corrections can be made for rotations, translations, or other motions of the subject. For example, if the patient moved 5 cm to the left and rotated 5 degrees to the right, the system may de-correct the corresponding imaging data by updating the position 5 cm to the right and rotating it 5 degrees to the left.

In some embodiments, the tracking data associated with the position and/or motion data is used to de-correct the raw imaging data. For example, instead of inverting the positions and/or motions of the subject being scanned received from a detector processing interface, the system may invert the raw motion tracking data from the one or more detectors to then generate new inverted position and/or motion data associated with the scan. In some embodiments, generating the de-corrected raw imaging data is performed using the same processes that are used in a post-processing motion-correction system. For example, the inverted position and/or motion data may be applied to the raw imaging data in a post-processing motion-correction system, however, the inverted positions and/or motion data generates de-corrected raw imaging data when the original raw imaging data was generated using prospective motion correction.

In block 516, the system reconstructs and outputs the de-corrected images. The reconstruction process may be the same performed in block 510 and may be performed by the same systems or modules, however, the raw data has been updated to remove the effects of the prospective motion compensation used when acquiring the raw imaging data. The motion corrected and de-corrected images may be presented together for comparison. For example, the images may be presented on a display screen, printed, or stored for later access. In some embodiments, a pictorial or visual representation of the tracked motion may also be displayed or otherwise presented along with the images. Such representation may be similar to as shown in, for example, FIGS. 18 and 21-23C of the '546 Application.

In some embodiments the de-corrected and motion-corrected images may be displayed (side by side or otherwise) for slice by slice comparison to the scanner operator or doctor or other user of the system. For example, the system may be configured to enable a doctor to scroll through a synchronized set of images or slices, such that the de-corrected and motion-corrected images or slices from the same corresponding point in time are always displayed together. In some embodiments, the system may be configured to enable the user to scroll through the images or slices independently such that the de-corrected and motion-corrected images or slices may be from a different point in time.

In some embodiments, the system displays the motion-corrected and de-corrected images with a label indicating which set of imaging data is being shown. For example, the de-corrected images could be displayed with a label that states it is de-corrected imaging data. When comparing the images, the operator or doctor or other use may be enabled to save the better imaging data (or to indicate a preference for the motion-corrected or de-corrected data). In some embodiments, the doctor saves the entire 2D or 3D representation of the scanned area; however, in some embodiments, the doctor can also save slices individually to generate composite data, wherein the best image quality is used from each individual slice. In such embodiments, each individual slice may be labelled such that the individual slices of the composite scanned images are identified as motion-corrected or de-corrected. For example, the system may be configured to enable a user to generate a composite or merged set of scanned data or images that is created by interlacing or merging motion corrected and motion de-corrected images or slices into the same set of data (which may be created as a new set of data, or may be an edited version of existing data). In some embodiments, the system is configured to change the stored data by removing and/or adding individual slices. In some embodiments, the system is configured to generate a new set of data that comprises at least one of a motion corrected or de-corrected slice or image for each point in time of the subject scan. In some embodiments, the system is configured to generate or update header information for the dataset and/or individual images or slices, such as to indicate that a composite data set is being used, whether each slice or image has been motion corrected, and/or the like.

Figure 5B:
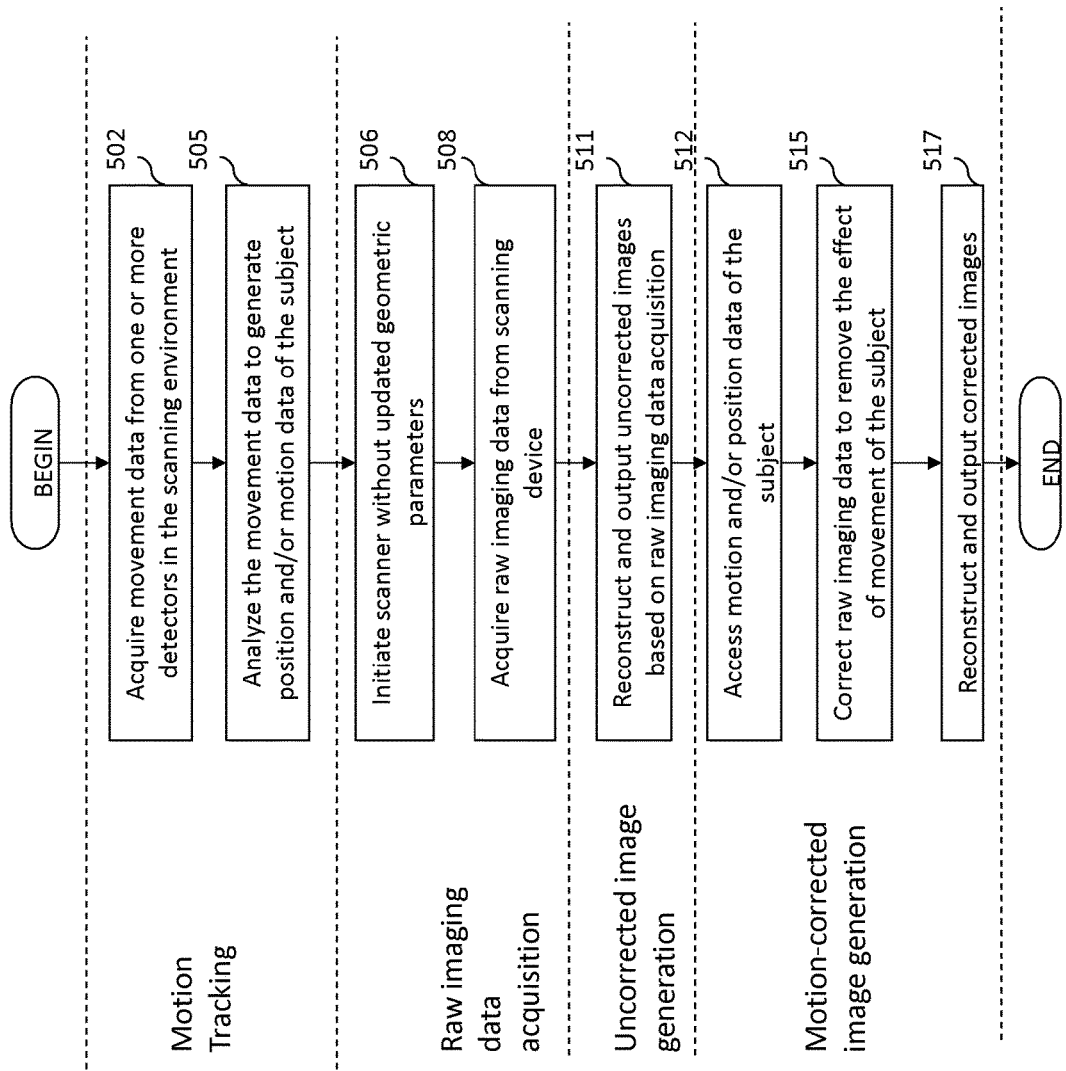

FIG. 5B illustrates a process flow of an example of embodiments of one or more methods of generating corrected and de-corrected images without prospective motion compensation by using, for example, post-processing techniques. The process is similar to the process described in reference to FIG. 5A. For example, blocks 502, 506, and 508 may each be performed in the same or a similar manner as described in reference to the processes in FIG. 5A. In block 505, the system uses the motion tracking data provided in block 502 to generate position and/or motion data about the subject. This data is stored for post-processing motion correction alongside (or otherwise associated with) the corresponding raw imaging data acquired by the scanner.

In blocks 506 and 508, the scanner scans the subject to acquire raw imaging data about the subject. Then, moving on to block 511, the system reconstructs the raw imaging data into final images. The reconstruction of the raw imaging data in this case generates de-corrected (or uncorrected) images because the scanning controller did not apply prospective motion control to the scanner while acquiring data. Therefore, motion artifacts from the process may be present in the reconstructed images.

In block 512, the system accesses motion and/or position data of the subject stored by the system in block 505. For example, the position of the subject may be stored as each scanning step is performed by the scanner. Moving to block 515, the raw imaging data is processed to remove the effects of the motion of the subject using one or more of a variety of potential processing algorithms. For example, if the position of the subject is shown to be 5 degrees rotated clockwise with respect to a baseline position, the raw image data may be processed, either before reconstruction or concurrently with reconstruction, to compensate for that positioning, eliminating or reducing any motion artifacts that would otherwise appear in the reconstructed images. When applied to each scan in the raw imaging data, a motion corrected set of raw imaging data is generated. In block 517, the system reconstructs and outputs the corrected images using the corrected raw imaging data. As noted above, in some embodiments, image reconstruction may occur concurrently with motion correction or compensation. The motion corrected and de-corrected images may be provided together for review.

Figure 6A:
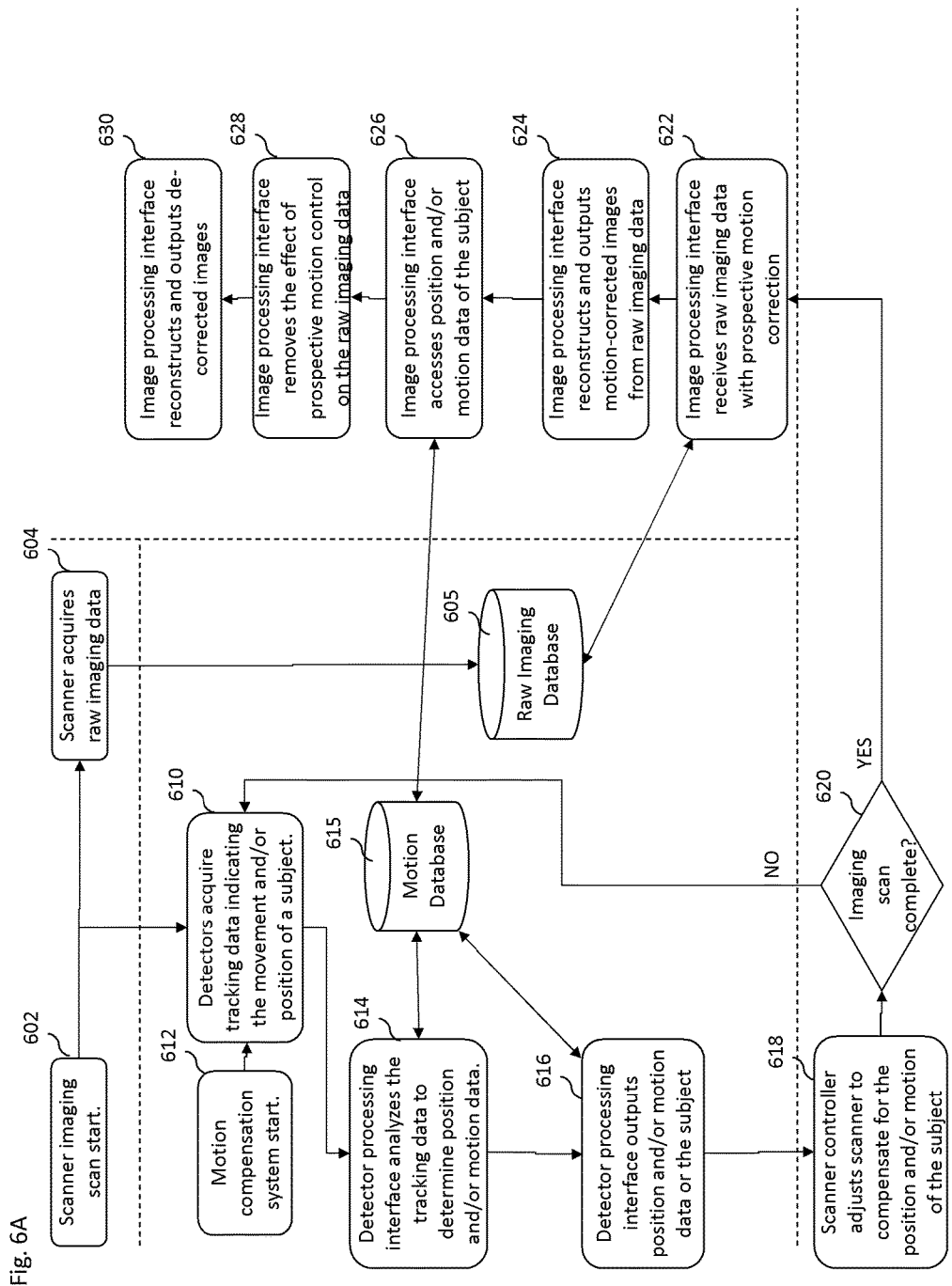
FIGS. 6A and 6B depict additional embodiments of a process flow diagram illustrating examples of motion correction removal processes.
Figure 6B:
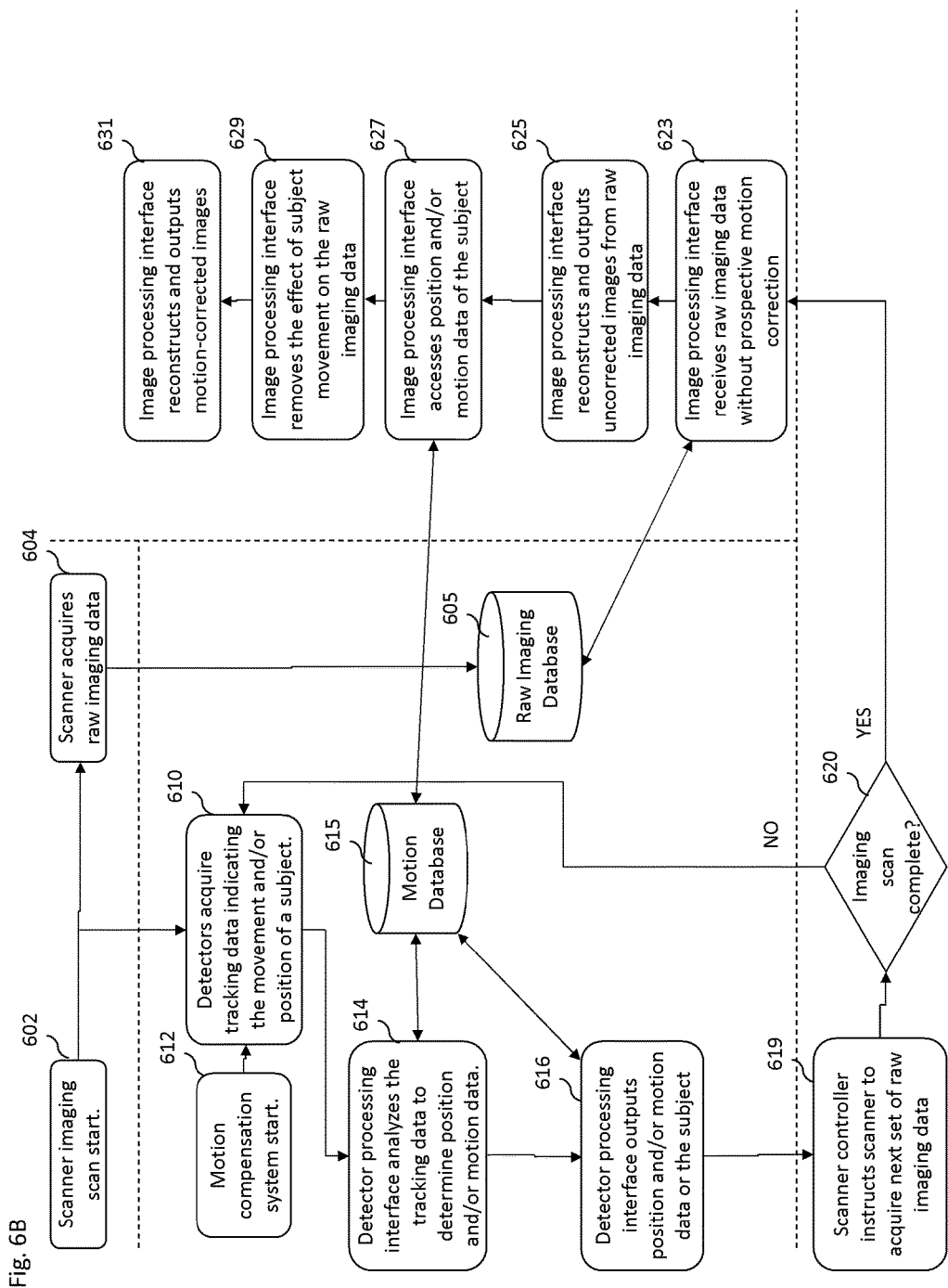

FIGS. 6A and 6B illustrate more detailed embodiments of processes for generating de-corrected images during a scanning process. Beginning in blocks 602 and 612, the scanning process and motion compensation processes begin. In starting the motion compensation process, a baseline position of the subject may be taken, from which the position of the subject during the scanning process can be compared. In block 610, one or more detectors acquire raw movement or tracking data indicating the movements and/or position of a subject (for example, one or more images created by one or more cameras, distance measurements, and/or a variety of other pieces of information that may be used to track object motion, as described in more detail above). The movement or tracking data may then be used by a detector processing interface in block 614 to determine the position of the subject compared to a baseline position. For example the detector processing interface may be as described with reference to FIGS. 1 and 2 above, and may include one or more tracking controllers and tracking combination interfaces to determine a position of the subject. In block 616, the detector processing interface outputs the position of the subject compared to the baseline position. The position may, for example, be stored as a matrix showing the position compared to the baseline, may be stored according to translations and rotations of the subject compared to the baseline, and/or may be stored in another format. The output including the position is stored in a motion database 615 for later use. The position data is also used by a scanner controller in block 618 to adjust the scanner to compensate for the updated position or motion of the subject. The scanner controller can then direct the scanner to acquire prospective motion compensated raw imaging data based on the position of the subject.

In block 604, the scanner acquires raw imaging data. The acquired data is compensated based on the tracked position of the subject by the scanner controller. Therefore, 2D or 3D data is generated with the position stored with respect to the position within the patient or subject instead of just to the position of the scanner. The raw imaging data is stored in a raw imaging database 605. The processes performed in blocks 610, 614, 616, and 618 are repeated by the system for each iteration of the scanner acquiring raw imaging data in block 604. For example, after outputting the position and/or motion data in block 616, and the scanning controller adjust the scanner in block 618, the system determines if the imaging scan is complete in block 620. If the scan is complete, the system moves on to block 622. If the scan is not complete, the motion compensation system repeats the processes of acquiring and analyzing the movement and/or position data of the subject.

In block 622, the image processing interface receives raw imaging data from raw imaging database 605. The raw imaging data was generated by the scanner with prospective motion compensation. As such, in block 624, the image processing interface reconstructs and outputs motion-corrected images directly from the raw imaging data.

In block 626, the image processing interface accesses position and/or motion data of the subject from motion database 615. Moving on to block 628, the image processing interface removes the effects of the prospective motion control from the raw imaging data. For example, the positions used to compensate the scanning acquisition process may be inverted by the motion de-corrected images generator. The inverted positions may then be used to change the positions in the raw imaging data to remove the effect of the previously made corrections. Another example process for de-correcting images is described further below with reference to FIG. 7. In block 630, the image processing interface reconstructs the de-corrected images from the de-corrected raw imaging data.

In some embodiments, the processes shown in FIG. 6A may include fewer or additional steps. For example, the system may only generate de-corrected images and not motion corrected images. In addition, the processes performed in blocks 622 and 624 may be performed in parallel with those performed in block 626, 628, and 630, to reconstruct motion corrected and motion de-corrected images at the same time. Furthermore, while the processes illustrated in FIG. 6A illustrate reconstruction and/or de-correction of raw imaging data occurring after the scanning process has been completed, in some embodiments, the processes may occur in parallel. For example, as the scanner is scanning images with prospective motion correction, the image processing interface may be reconstructing the images into motion-corrected images in block 624, and performing the processes to generate de-corrected images.

FIG. 6B illustrates similar processes to those shown in FIG. 6A, only without using prospective motion control. The processes used for acquiring tracking data, generating motion and/or position data, and storing that information are the same as in FIG. 6B. The first difference in the processes is in block 619. The scanner controller in FIG. 6B does not compensate for the updated position of the subject. Instead, in block 604, when the scanner acquires raw imaging data, the data is not compensated for motion.

The next difference from the processes performed in the embodiment illustrated in FIG. 6A, is the processing of the raw imaging data in blocks 623, 625, 627, 629, and 631 of FIG. 6B. In block 623, the image processing interface receives raw imagine data without prospective motion correction. The raw imaging data is then reconstructed in block 625 as de-corrected or uncorrected images, potentially having one or more motion artifacts based on the subject's movements. In block 627, the image processing interface accesses position and/or motion data of the subject, which in block 629 is used to remove the effects of the subjects movement from the raw imaging data. In block 631, the motion corrected raw imaging data is reconstructed into motion corrected images to provide to a user. The reconstructed motion corrected and de-corrected images may be provided together for comparison and/or review.

FIG. 7 illustrates a process for generating de-corrected images from raw imaging data as used in some embodiments. In block 702, the system acquires raw imaging data. For example, raw imaging data is provided to the image processing system by a scanning device. The raw imaging data received has been generated with prospective motion compensation such that when reconstructed motion artifacts should be minimized. In block 704, the system acquires position and/or motion data from a motion database. The position data may be stored in a separate database from the raw imaging data or it may be stored in the same database, file, or location. For example, in some embodiments, each iteration of a scan from the scanner may include data of the corresponding position of the subject. The position of the subject indicated by the position data may in some embodiments be based on the change in position compared to a baseline position. For example the data may have information related to or describing the subject's movement in up to 6 degrees of freedom from the original position when scanning began.

In block 706, the system generates inverse motion data for each position or motion recorded in the motion database. For example, if the position of the subject corresponding to a scan indicates the position of the subject was rotated or translated in one direction, the system may generate inverse motion data indicating that the subject was rotated or translated in the opposite direction. This inverse motion data can then be used to reverse the effects of the prospective motion control from the scan.

As an example, in some embodiments, the rotational component of a subject's motion data may be stored as a matrix of values indicating the subject's movements. In one embodiment, the system stores the position of the subject as a set of quaternion rotation matrices. Taking the inverse of the quaternion matrix then provides inverse motion data which can be used to de-correct the prospective motion compensation from the raw imaging data. While using quaternion matrices has advantages, rotation matrices may provide a similar mechanism for de-correcting the raw imaging data. For example, for a given unit quaternion (qr,qx,qy,qz)=(q1,q2,q3,q4) the corresponding rotation matrix dcm (discrete cosine matrix) is calculated using the following definition.

$$dcm(1,1)=q(1)\char`\^2+q(2)\char`\^2-q(3)\char`\^2-q(4)\char`\^2;$$

$$dcm(1,2)=2\cdot*(q(2)\cdot*q(3)-q(1)\cdot*q(4));$$

$$dcm(1,3)=2\cdot*(q(2)\cdot*q(4)+q(1)\cdot*q(3));$$

$$dcm(2,1)=2\cdot*(q(2)\cdot*q(3)+q(1)\cdot*q(4));$$

$dcm(2,2)=q(1).^2-q(2).^2+q(3).^2-q(4).^2;$ $dcm(2,3)=2\cdot *(q(3)\cdot *q(4)-q(1)\cdot *q(2));$ $dcm(3,1)=2\cdot *(q(2)\cdot *q(4)-q(1)\cdot *q(3));$ $dcm(3,2)=2\cdot *(q(3)\cdot *q(4)+q(1)\cdot *q(2));$ $dcm(3,3)=q(1).^2-q(2).^2-q(3).^2+q(4).^2;$ Thus, as an example, the quaternion encoding a pure sagittal slice orientation Orientation[0]=(−0.500000 0.500000 −0.500000, 0.500000) as in the log file and (qr,qx,qy,qz)=(0.500000,−0.500000,0.500000,−0.500000) is transformed to the following rotation matrix:

$$R = \begin{pmatrix} 0 & 0 & 1 \\ -1 & 0 & 0 \\ 0 & -1 & 0 \end{pmatrix}$$

In block 708, the system applies the inverse motion data to the corresponding raw imaging data to generate de-corrected raw imaging data. For example, the position of each scan, slice, or other imaging data may be rotated or translated according to the inverse motion data associated with the imaging data. The imaging data is therefore placed in a position approximating the position it would have corresponded to if not for the prospective motion control. Then, in block 710 de-corrected images are generated from the de-corrected raw imaging data. The reconstruction process may occur as it normally would for any raw imaging data received from a scanner.

Testing of a Motion De-Correction System

Figure 8B:
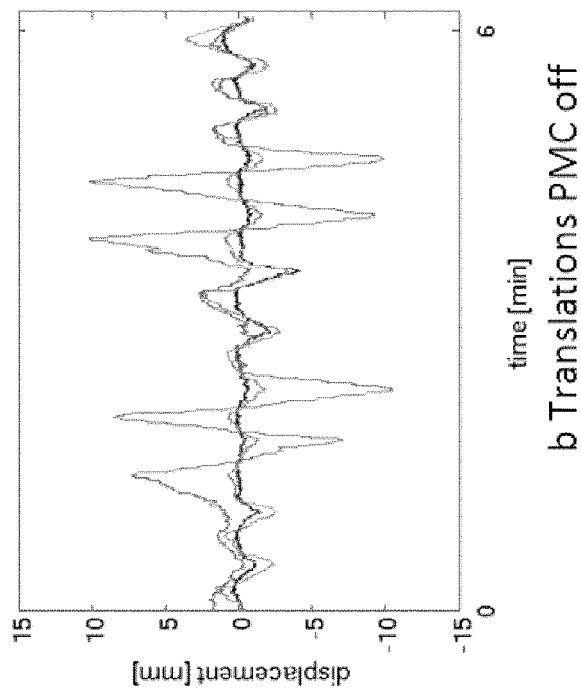
FIGS. 8A and 8B illustrate motion traces depicting data obtained during a motion tracking process.
Figure 8A:
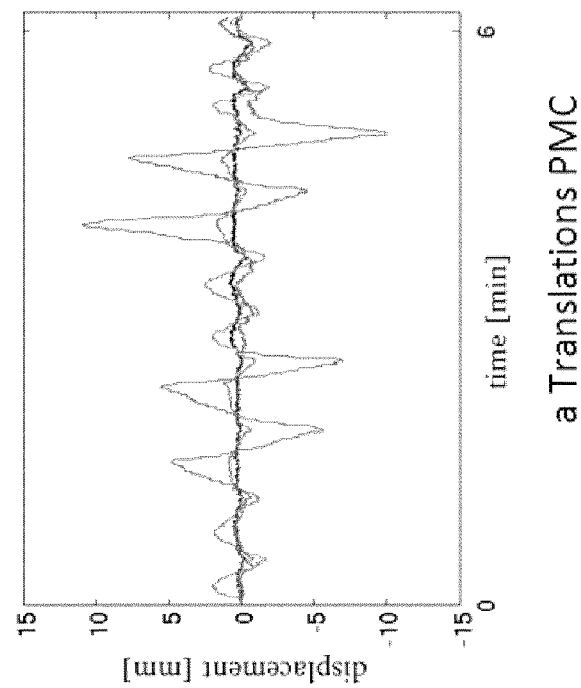

FIGS. 8-9 illustrate an example of a test performed utilizing one embodiment of a motion de-correction or motion compensation removal system. In this test, three MPRAGE scans (1.3×1.3×1.3 mm3, TR=2000 ms, TI=900 ms,) were acquired. In two of the scans the subject continuously performed nodding and shaking motion. FIGS. 8A and 8B display the motion traces (translations only) during a 6 minute scan with maximum amplitude around 20 mm and similar pattern for both scans. For a third and last scan the subject was told not to move and prospective motion correction was turned on (not shown). This serves as a baseline scan approximating what a clean scan would look like for each of the tests.

For the first scan with head motion (FIG. 8A) prospective motion correction was enabled. For the second scan (head motion according to FIG. 8B) prospective motion correction not applied, but the system was continuously logging the tracking, positions, and/or motion data of the subject and the camera frame numbers.

Results from the test can be seen in FIGS. 9A-9D. In FIG. 9A the base line image acquired from a stationary head pose is shown. In this first image, prospective motion correction was applied and resulted in a clean scan showing clear details. FIG. 6B illustrates an image from a scan with prospective motion correction applied, but with movement from the subject. In this example, the movement shown in FIG. 8A has been removed using prospective motion correction. FIG. 9D shows the case of a scan where the subject moved and prospective motion correction was not applied during the scanning process. The slow but rather pronounced head motion shown in FIG. 8B results in dramatic degradation of the image quality up to a point where it becomes non-diagnostic or cannot be used for gray/white matter segmentation.

The motion traces from FIG. 8A were then used to undo the effects of the prospective motion correction with the result (FIG. 9C) showing how the image would have looked if prospective motion correction switched off. In some embodiments, the "undoing" process can be similar to the processes illustrated in FIGS. 3-9, as further described above. The "de-corrected" reconstruction in FIG. 9C shows similar artifacts as the uncorrected image in FIG. 9D. The different motion traces of both runs are likely to be responsible for the differences in the artifacts visible. That is, because the motion of the subjects was not exactly the same, the degradation in the uncorrected images shown in FIG. 9D and the degradation of the de-corrected images shown in FIG. 9C are not exactly the same.

Computing System

Figure 10:
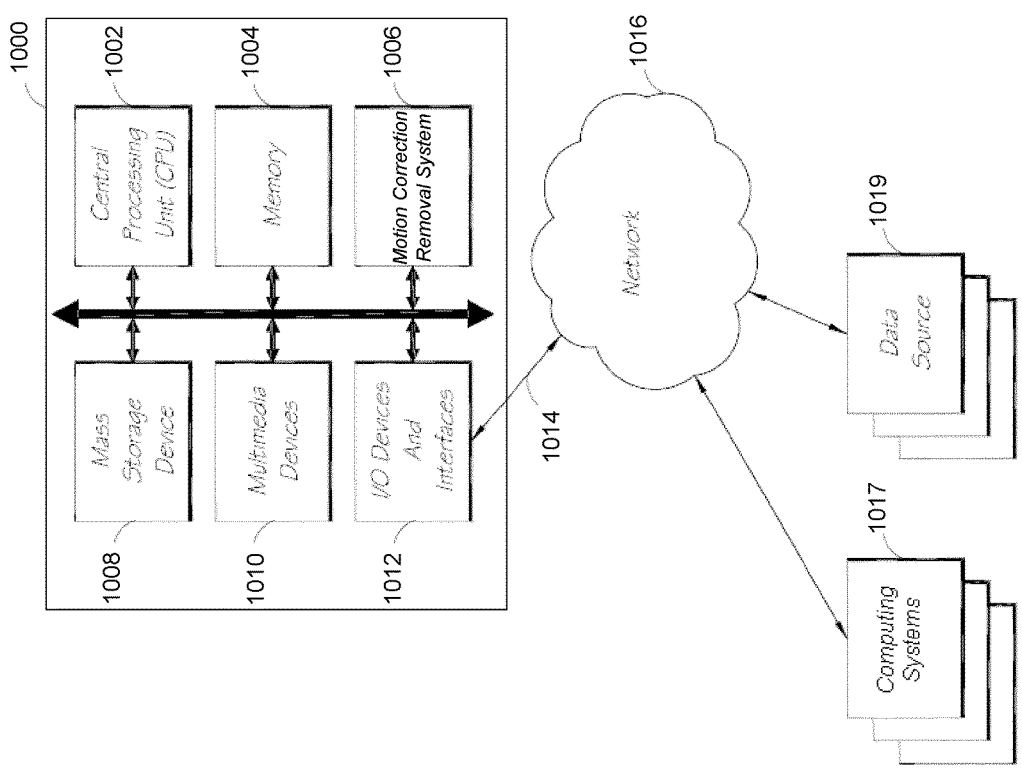
FIG. 10 is a block diagram depicting an embodiment of a computer hardware system configured to run software for implementing one or more embodiments of the systems described herein.

FIG. 10 is a block diagram depicting an embodiment of a computer hardware system configured to run software for implementing one or more embodiments of the motion correction removal systems described herein.

In some embodiments, the computer clients and/or servers described above take the form of a computing system 1000 illustrated in FIG. 10, which is a block diagram of one embodiment of a computing system that is in communication with one or more computing systems 1017 and/or one or more data sources 1019 via one or more networks 1016. The computing system 1000 may be used to implement one or more of the systems and methods described herein. In addition, in one embodiment, the computing system 1000 may be configured to manage access or administer a software application. While FIG. 10 illustrates one embodiment of a computing system 1000, it is recognized that the functionality provided for in the components and modules of computing system 1000 may be combined into fewer components and modules or further separated into additional components and modules.

Motion Correction Removal System Module

In one embodiment, the computing system 1000 comprises a motion correction removal system 1006 that carries out the functions described herein with reference to removing prospective motion correction from images, including any one of techniques described above. The motion correction removal system 1006 and/or other modules may be executed on the computing system 1000 by a central processing unit 1002 discussed further below.

In general, the word "module," as used herein, refers to logic embodied in hardware or firmware, or to a collection of software instructions, possibly having entry and exit points, written in a programming language, such as, for example, COBOL, CICS, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

Computing System Components

In one embodiment, the computing system 1000 also comprises a mainframe computer suitable for controlling and/or communicating with large databases, performing high volume transaction processing, and generating reports from large databases. The computing system 1000 also comprises a central processing unit ("CPU") 1002, which may comprise a conventional microprocessor. The computing system 1000 further comprises a memory 1004, such as random access memory ("RAM") for temporary storage of information and/or a read only memory ("ROM") for permanent storage of information, and a mass storage device 1008, such as a hard drive, diskette, or optical media storage device. Typically, the modules of the computing system 1000 are connected to the computer using a standards based bus system. In different embodiments, the standards based bus system could be Peripheral Component Interconnect (PCI), Microchannel, SCSI, Industrial Standard Architecture (ISA) and Extended ISA (EISA) architectures, for example.

The computing system 1000 comprises one or more commonly available input/output (I/O) devices and interfaces 1012, such as a keyboard, mouse, touchpad, and printer. In one embodiment, the I/O devices and interfaces 1012 comprise one or more display devices, such as a monitor, that allows the visual presentation of data to a user. More particularly, a display device provides for the presentation of GUIs, application software data, and multimedia presentations, for example. In one or more embodiments, the I/O devices and interfaces 1012 comprise a microphone and/or motion sensor that allow a user to generate input to the computing system 1000 using sounds, voice, motion, gestures, or the like. In the embodiment of FIG. 10, the I/O devices and interfaces 1012 also provide a communications interface to various external devices. The computing system 1000 may also comprise one or more multimedia devices 1010, such as speakers, video cards, graphics accelerators, and microphones, for example.

Computing System Device/Operating System

The computing system 1000 may run on a variety of computing devices, such as, for example, a server, a Windows server, a Structure Query Language server, a Unix server, a personal computer, a mainframe computer, a laptop computer, a tablet computer, a cell phone, a smartphone, a personal digital assistant, a kiosk, an audio player, an e-reader device, and so forth. The computing system 1000 is generally controlled and coordinated by operating system software, such as z/OS, Windows 95, Windows 98, Windows NT, Windows 2000, Windows XP, Windows Vista, Windows 7, Windows 8, Linux, BSD, SunOS, Solaris, Android, iOS, BlackBerry OS, or other compatible operating systems. In Macintosh systems, the operating system may be any available operating system, such as MAC OS X. In other embodiments, the computing system 1000 may be controlled by a proprietary operating system. Conventional operating systems control and schedule computer processes for execution, perform memory management, provide file system, networking, and I/O services, and provide a user interface, such as a graphical user interface ("GUI"), among other things.

Network

In the embodiment of FIG. 10, the computing system 1000 is coupled to a network 1016, such as a LAN, WAN, or the Internet, for example, via a wired, wireless, or combination of wired and wireless, communication link 1014. The network 1016 communicates with various computing devices and/or other electronic devices via wired or wireless communication links. In the embodiment of FIG. 10, the network 1016 is communicating with one or more computing systems 1017 and/or one or more data sources 1019.

Access to the motion correction removal system 1006 of the computer system 1000 by computing systems 1017 and/or by data sources 1019 may be through a web-enabled user access point such as the computing systems' 1017 or data source's 1019 personal computer, cellular phone, smartphone, laptop, tablet computer, e-reader device, audio player, or other device capable of connecting to the network 1016. Such a device may have a browser module that is implemented as a module that uses text, graphics, audio, video, and other media to present data and to allow interaction with data via the network 1016.

The browser module may be implemented as a combination of an all points addressable display such as a cathode-ray tube (CRT), a liquid crystal display (LCD), a plasma display, or other types and/or combinations of displays. In addition, the browser module may be implemented to communicate with input devices 1012 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 1000 may comprise a physical or logical connection established between a remote microprocessor and a mainframe host computer for the express purpose of uploading, downloading, or viewing interactive data and databases on-line in real time. The remote microprocessor may be operated by an entity operating the computer system 1000, including the client server systems or the main server system, an/or may be operated by one or more of the data sources 1019 and/or one or more of the computing systems 1017. In some embodiments, terminal emulation software may be used on the microprocessor for participating in the micro-mainframe link.

In some embodiments, computing systems 1017 who are internal to an entity operating the computer system 1000 may access the motion correction removal system 1006 internally as an application or process run by the CPU 1002.

User Access Point

In an embodiment, a user access point or user interface comprises a personal computer, a laptop computer, a tablet computer, an e-reader device, a cellular phone, a smartphone, a GPS system, a Blackberry® device, a portable computing device, a server, a computer workstation, a local area network of individual computers, an interactive kiosk, a personal digital assistant, an interactive wireless communications device, a handheld computer, an embedded computing device, an audio player, or the like.

Other Systems

In addition to the systems that are illustrated in FIG. 10, the network 1016 may communicate with other data sources or other computing devices. The computing system 1000 may also comprise one or more internal and/or external data sources. In some embodiments, one or more of the data repositories and the data sources may be implemented using a relational database, such as DB2, Sybase, Oracle, CodeBase and Microsoft® SQL Server as well as other types of databases such as, for example, a flat file database, an entity-relationship database, and object-oriented database, and/or a record-based database.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. For all of the embodiments described herein the steps of the methods need not be performed sequentially. Thus, it is intended that the scope of the present inventions herein disclosed should not be limited by the particular disclosed embodiments described above.

What is claimed is:

1. A system for generating motion de-corrected images in conjunction with a biomedical imaging scan, the system comprising:
    a biomedical image scanner;
    one or more detectors configured to capture motion data for an object being scanned by the biomedical image scanner;
    one or more computer readable storage devices configured to store a plurality of computer executable instructions: and
    one or more hardware computer processors in communication with the one or more computer readable storage devices and configured to execute the plurality of computer executable instructions causing the system to:
    use the one or more detectors to capture motion data for the object while scanning the object with the biomedical image scanner;
    generate motion tracking data from the motion data, the motion tracking data indicating a position of the object being scanned by the biomedical image scanner;
    adjust the biomedical image scanner using the motion tracking data to compensate in real time for object motions while scanning the object to generate raw image data, such that the raw image data generated by the biomedical image scanner can be reconstructed directly into motion-corrected images;
    reconstruct motion-corrected images directly from the raw image data; and
    generate, based on the raw image data and the motion tracking data, de-corrected image data representative of what the scanner would produce had the scanner not compensated for motion; and
    reconstruct de-corrected images based on the de-corrected image data.

2. The system of claim 1, wherein the de-corrected images are generated by inverting the motion tracking data and applying the inverted motion tracking data to the raw image data to generate de-corrected image data.

3. The system of claim 1, wherein the one or more hardware computer processors executing the plurality of computer executable instructions further causes the system to:
    transmit the motion-corrected images and the de-corrected images to an electronic display for simultaneous display to a user.

4. The system of claim 3, wherein the system further comprises an electronic display device, wherein the motion-corrected images and the de-corrected images are configured to be displayed on the electronic display device.

5. The system of claim 1, wherein the motion de-corrected images are generated using a regridding process to remove the effects of compensating for motions of the object being scanned.

6. The system of claim 1, wherein the motion de-corrected images are generated using a SENSE algorithm to de-correct the raw image data using the motion tracking data.

7. The system of claim 1, further comprising a marker configured to be coupled to the object during scanning, wherein the one or more detectors track the motion of the marker to generate motion tracking data.

8. The system of claim 1, wherein the motion tracking data is generated by at least one of comparing the position of the object being scanned to a baseline position, and comparing a motion of the object in comparison to a previous position of the object.

9. The system of claim 1, wherein the one or more detectors are at least partially embedded in a wall of the biomedical imaging scanner.

10. The system of claim 1, wherein the biomedical imaging scanner comprises a wall positioned between an MRI magnet and a bore for positioning therein of the object, the wall comprising a first side proximal to the bore and a second side distal to the bore, wherein the one or more detectors are positioned in a cavity adjacent the second side of the wall.

11. The system of claim 1, wherein the scanner is one of an MRI or a CT scanning system.

12. The system of claim 1, wherein the motion tracking data is generated based at least in part on tracking one or more anatomical landmarks.

13. The system of claim 1, wherein the motion tracking data comprises one or more quaternion rotation matrices representing the position of the object being scanned.

14. The system of claim 13, wherein the de-corrected image data is generated by inverting the one or more quaternion rotation matrices and applying the inverted one or more quaternion rotation matrices to the raw image data.

15. The system of claim 1, wherein the one or more hardware computer processors executing the plurality of computer executable instructions further causes the system to generate composite data, wherein the composite data comprises one or more slices of the motion corrected images and one or more slices of the de-corrected images.

16. The system of claim 15, wherein the one or more hardware computer processors executing the plurality of computer executable instructions further causes the system to generate header information for each slice of the composite data, wherein the header information indicates whether each slice of the composite data corresponds to motion corrected images or de-corrected images.

17. A computer comprising a processor and a non-transitory computer readable medium, wherein the medium comprises instructions executable by the processor, the instructions comprising:
   tracking motion of an object while scanning the object with a biomedical imaging scanner;
   generating motion tracking data indicating a position of the object while being scanned;
   adjusting the biomedical imaging scanner with the motion tracking data to compensate in real time for object motion while scanning the object to generate raw image data, such that raw image data generated by the scanner can be reconstructed directly into motion-corrected images;
   reconstructing motion-corrected images directly from the raw image data;
   inverting the motion tracking data to generate inverted motion tracking data; and
   applying the inverted motion tracking data to the raw image data to generate de-corrected image data representative of what the scanner would produce had the scanner not compensated for motion
   reconstructing de-corrected images from the de-corrected image data.

18. The computer of claim 17, wherein the instructions further comprise:
   transmitting the motion-corrected images and the de-corrected images to an electronic display for simultaneous display to a user.

19. The computer of claim 18, wherein the instructions further comprise:
   transmitting data enabling display, simultaneously with the motion-corrected and de-corrected images, of a pictorial representation of the motion tracking data.

20. The computer of claim 17, wherein the step of tracking motion comprises tracking motion of a marker coupled to the object.

21. The computer of claim 17, wherein generating the motion tracking data comprises at least one of comparing the position of the object being scanned to a baseline position, and comparing a motion of the object in comparison to a previous position of the object.

22. The computer of claim 17, wherein compensating in real time for object motion further comprises updating geometric parameters of the scanner based on an updated position of the object being scanned.

23. The computer of claim 17, wherein the biomedical imaging scanner scans the object and generates raw image data using a process comprising:
   exciting nuclei within the object being scanned;
   applying a magnetic field gradient across the object being scanned; and
   receiving, at a receiver coil of the biomedical imaging scanner, radiofrequency signals indicating one or more features of the object being scanned.

24. The computer of claim 17, wherein the motion tracking data is generated based at least in part on tracking one or more anatomical landmarks.

25. The computer of claim 17, wherein the motion tracking data comprises one or more quaternion rotation matrices representing the position of the object being scanned.

26. The computer of claim 17, wherein the inverted motion tracking data comprises one or more inverted quaternion rotation matrices, wherein the quaternion rotation matrices represent the position of the object being scanned.

27. The computer of claim 17, wherein the instructions further comprise generating composite data, wherein the composite data comprises one or more slices of the motion corrected images and one or more slices of the de-corrected images.

28. The computer of claim 27, wherein the instructions further comprise generating header information for each slice of the composite data, wherein the header information indicates whether each slice of the composite data corresponds to motion corrected images or de-corrected images.

* * * * *